US010344303B2

(12) United States Patent
Retsina et al.

(10) Patent No.: US 10,344,303 B2
(45) Date of Patent: Jul. 9, 2019

(54) HYDROTHERMAL-MECHANICAL CONVERSION OF LIGNOCELLULOSIC BIOMASS TO ETHANOL OR OTHER FERMENTATION PRODUCTS

(71) Applicant: API Intellectual Property Holdings, LLC, Minnetrista, MN (US)

(72) Inventors: Theodora Retsina, Atlanta, GA (US); Vesa Pylkkanen, Atlanta, GA (US); Steven R. Rutherford, Peachtree City, GA (US); Jean-Pierre Monclin, Lafayette, LA (US)

(73) Assignee: GRANBIO INTELLECTUAL PROPERTY HOLDINGS, LLC, Atlanta, GA (US)

( * ) Notice: Subject to any disclaimer, the term of this patent is extended or adjusted under 35 U.S.C. 154(b) by 2 days.

(21) Appl. No.: 15/957,480

(22) Filed: Apr. 19, 2018

(65) Prior Publication Data

US 2018/0237806 A1 Aug. 23, 2018

Related U.S. Application Data

(63) Continuation of application No. 15/297,839, filed on Oct. 19, 2016, now abandoned, which is a continuation of application No. 15/047,608, filed on Feb. 18, 2016, now abandoned.

(60) Provisional application No. 62/150,643, filed on Apr. 21, 2015, provisional application No. 62/197,160, filed on Jul. 27, 2015, provisional application No. 62/240,461, filed on Oct. 12, 2015, provisional application No. 62/263,292, filed on Dec. 4, 2015, provisional application No. 62/267,533, filed on Dec. 15, 2015, provisional application No. 62/118,335, filed on Feb. 19, 2015, provisional application No. 62/141,664, filed on Apr. 1, 2015.

(51) Int. Cl.
*D21C 3/00* (2006.01)
*C12P 7/14* (2006.01)
*D21C 1/02* (2006.01)
*D21C 9/00* (2006.01)

(52) U.S. Cl.
CPC .............. *C12P 7/14* (2013.01); *D21C 1/02* (2013.01); *D21C 3/00* (2013.01); *D21C 9/00* (2013.01); *C12P 2201/00* (2013.01); *C12P 2203/00* (2013.01); *Y02E 50/16* (2013.01)

(58) Field of Classification Search
None
See application file for complete search history.

(56) References Cited

U.S. PATENT DOCUMENTS

| 3,652,387 | A | | 3/1972 | Wilder | |
|---|---|---|---|---|---|
| 4,652,374 | A | * | 3/1987 | Cohen | .................... C12M 21/04 |
| | | | | | 210/603 |
| 2008/0026431 | A1 | | 1/2008 | Saito et al. | |
| 2009/0098616 | A1 | * | 4/2009 | Burke | ........................ C12P 7/04 |
| | | | | | 435/99 |
| 2009/0224086 | A1 | | 9/2009 | Hata | |
| 2010/0297742 | A1 | | 11/2010 | Solheim et al. | |
| 2011/0143411 | A1 | | 6/2011 | Yuan et al. | |
| 2011/0207177 | A1 | * | 8/2011 | Sugiura | ..................... C12P 7/10 |
| | | | | | 435/72 |
| 2011/0315541 | A1 | | 12/2011 | Xu | |
| 2012/0006320 | A1 | | 1/2012 | Nguyen | |
| 2013/0143290 | A1 | | 6/2013 | Narendranath | |
| 2013/0158308 | A1 | | 6/2013 | Powell et al. | |
| 2014/0234936 | A1 | * | 8/2014 | Kusuda | ..................... C12P 7/10 |
| | | | | | 435/165 |
| 2014/0370551 | A1 | | 12/2014 | Retsina et al. | |

FOREIGN PATENT DOCUMENTS

WO  WO-2013046624 A1 * 4/2013 ................ C12P 7/10

OTHER PUBLICATIONS

Written Opinion of the International Searching Authority (ISA/US), PCT/US2016/018556, dated May 3, 2016, 10 pages.
Batalha et al., "Production of fermentable sugars from sugarcane bagasse by enzymatic hydrolysis after autohydrolysis and mechanical refining", Bioresource Technology 180 (2015) 97-105.
Ertas et al., "Enzymatic hydrolysis of autohydrolyzed wheat straw followed by refining to produce fermentable sugars", Bioresource Technology 152 (2014) 259-266.
Heitz et al., "Generalized Correlations for the Aqueous Liquefaction of Lignocellulosics", The Canadian Journal of Chemical Engineering, vol. 64, Aug. 1986, pp. 647-650.
Hideno et al., "Combination of hot compressed water treatment and wet disk milling for high sugar recovery yield in enzymatic hydrolysis of rice straw", Bioresource Technology 104 (2012) 743-748.
Inoue et al., "Combining hot-compressed water and ball milling pretreatments to improve the efficiency of the enzymatic hydrolysis of eucalyptus", Biotechnology for Biofuels 2008, 1:2.
Kumagai et al., "Simultaneous saccharification and fermentation and a consolidated bioprocessing for Hinoki cypress and Eucalyptus after fibrillation by steam and subsequent wet-disk milling", Bioresource Technology 162 (2014) 89-95.

(Continued)

*Primary Examiner* — Thane Underdahl
(74) *Attorney, Agent, or Firm* — O'Connor & Company; Ryan P. O'Connor

(57) ABSTRACT

A low-cost process is provided to render lignocellulosic biomass accessible to cellulase enzymes, to produce fermentable sugars. Some variations provide a process to produce ethanol from lignocellulosic biomass (such as sugarcane bagasse or corn stover), comprising introducing a lignocellulosic biomass feedstock to a single-stage digestor; exposing the feedstock to a reaction solution comprising steam or liquid hot water within the digestor, to solubilize the hemicellulose in a liquid phase and to provide a cellulose-rich solid phase; refining the cellulose-rich solid phase, together with the liquid phase, in a mechanical refiner, thereby providing a mixture of refined cellulose-rich solids and the liquid phase; enzymatically hydrolyzing the mixture in a hydrolysis reactor with cellulase enzymes, to generate fermentable sugars; and fermenting the fermentable sugars to produce ethanol. Many alternative process configurations are described. The disclosed processes may be employed for other fermentation products.

18 Claims, 10 Drawing Sheets

(56) References Cited

OTHER PUBLICATIONS

Lee et al., "Increase in enzyme accessibility by generation of nanospace in cell wall supramolecular structure", Bioresource Technology 101 (2010) 7218-7223.

Sasaki et al., "Mechanical milling and membrane separation for increased ethanol production during simultaneous saccharification and co-fermentation of rice straw by xylose-fermenting *Saccharomyces cerevisiae*", Bioresource Technology 185 (2015) 263-268.

Weiqi et al., "Combination of liquid hot water pretreatment and wet disk milling to improve the efficiency of the enzymatic hydrolysis of eucalyptus", Bioresource Technology 128 (2013) 725-730.

Zakaria et al., "Combined pretreatment using alkaline hydrothermal and ball milling to enhance enzymatic hydrolysis of oil palm mesocarp fiber", Bioresource Technology 169 (2014) 236-243.

Zakaria et al., "Hydrothermal and wet disk milling pretreatment for high conversion of biosugars from oil palm mesocarp fiber", Bioresource Technology 181 (2015) 263-269.

Zhu et al. "On energy consumption for size-reduction and yields from subsequent enzymatic saccharification of pretreated lodgepole pine", Bioresource Technology 101 (2010) 2782-2792.

\* cited by examiner

HYDROTHERMAL-MECHANICAL CONVERSION OF LIGNOCELLULOSIC BIOMASS TO ETHANOL OR OTHER FERMENTATION PRODUCTS

PRIORITY DATA

This patent application is a continuation application of U.S. patent application Ser. No. 15/297,839, filed Oct. 19, 2016, which is a continuation application of U.S. patent application Ser. No. 15/047,608, filed Feb. 18, 2016, which claims priority to U.S. Provisional Patent App. No. 62/118,335, filed Feb. 19, 2015; U.S. Provisional Patent App. No. 62/141,664, filed Apr. 1, 2015; U.S. Provisional Patent App. No. 62/150,643, filed Apr. 21, 2015; U.S. Provisional Patent App. No. 62/197,160, filed Jul. 27, 2015; U.S. Provisional Patent App. No. 62/240,461, filed Oct. 12, 2015; U.S. Provisional Patent App. No. 62/263,292, filed Dec. 4, 2015; and U.S. Provisional Patent App. No. 62/267,533, filed Dec. 15, 2015, each of which is hereby incorporated by reference herein.

FIELD OF THE INVENTION

The present invention generally relates to processes for preparing fermentable sugars and fermentation products from lignocellulosic biomass.

BACKGROUND OF THE INVENTION

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network.

Biomass refining (or biorefining) has become prevalent in the world's economy. Cellulose fibers and sugars, hemicellulose sugars, lignin, syngas, and derivatives of these intermediates are being utilized for chemical and fuel production. Integrated biorefineries are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint. Over the past few years, several commercial-scale biorefineries have been constructed, designed to convert lignocellulosic biomass such as corn stover, wheat straw, and sugarcane bagasse or straw into so-called second-generation ethanol.

However, there remains a need for improved conversion technologies to produce second-generation ethanol. What is needed is a low-cost, practical approach to render lignocellulosic biomass easily accessible to cellulase enzymes, to produce fermentable sugars.

SUMMARY OF THE INVENTION

The present invention addresses the aforementioned needs in the art. Some variations of the invention are known as GreenPower3+® technology or GP3+® technology, commonly assigned with the assignee of this patent application.

Some variations provide a process to produce a fermentation product (e.g., ethanol) from lignocellulosic biomass, the process comprising:

(a) introducing a lignocellulosic biomass feedstock to a single-stage digestor, wherein the feedstock contains cellulose, hemicellulose, and lignin;

(b) exposing the feedstock to a reaction solution comprising steam or liquid hot water within the digestor, to solubilize at least a portion of the hemicellulose in a liquid phase and to provide a cellulose-rich solid phase;

(c) refining the cellulose-rich solid phase, together with the liquid phase, in a mechanical refiner to reduce average particle size of the cellulose-rich solid phase, thereby providing a mixture comprising refined cellulose-rich solids and the liquid phase;

(d) enzymatically hydrolyzing the mixture in a hydrolysis reactor with cellulase enzymes, to generate fermentable sugars from the mixture, wherein the hydrolysis reactor includes one or more hydrolysis stages; and (e) fermenting at least some of the fermentable sugars in a fermentor to produce a fermentation product.

In some embodiments, the lignocellulosic biomass feedstock is selected from the group consisting of hardwoods, softwoods, sugarcane bagasse, sugarcane straw, energy cane, corn stover, corn cobs, corn fiber, and combinations thereof.

The lignocellulosic biomass feedstock may be pretreated, prior to step (a), using one or more techniques selected from the group consisting of cleaning, washing, presteaming, drying, milling, particle size-classifying, and combinations thereof.

In some embodiments, the reaction solution further comprises an acid, such as (but not limited to) acetic acid. In some embodiments, at least a portion of the reaction solution is introduced to the feedstock in a pre-impregnator prior to step (b).

Step (b) may include a digestor residence time from about 2 minutes to about 4 hours. In some embodiments, the digestor residence time is about 10 minutes or less. Step (b) may include a digestor temperature from about 150° C. to about 220° C., such as from about 180° C. to about 200° C. Step (b) may be conducted at a digestor liquid-solid weight ratio from about 1 to about 4, preferably about 2 or less. Step (b) may be conducted at a digestor pH from about 3 to about 5, such as from about 3.5 to about 4.5.

In some embodiments of the process, a blow tank is configured for receiving the cellulose-rich solid phase or the refined cellulose-rich solids at a pressure lower than the digestor pressure. The blow tank may be disposed downstream of the digestor and upstream of the mechanical refiner, i.e. between the digestor and refiner. Or the blow tank may be disposed downstream of the mechanical refiner. In certain embodiments, a first blow tank is disposed upstream of the mechanical refiner and a second blow tank is disposed downstream of the mechanical refiner. Optionally, vapor is separated from the blow tank(s). The vapor may be purged and/or condensed or compressed and returned to the digestor. In either case, heat may be recovered from at least some of the vapor.

The mechanical refiner may be selected from the group consisting of a hot-blow refiner, a hot-stock refiner, a blow-line refiner, a disk refiner, a conical refiner, a cylindrical refiner, an in-line defibrator, an extruder, a homogenizer, and combinations thereof.

The mechanical refiner may be operated at a refining pressure selected from about 1 bar to about 20 bar. In some embodiments, the refining pressure is about 3 bar or less. In some embodiment, the mechanical refiner is operated at or about at atmospheric pressure.

The mechanical refiner may operate at an electrical load from about 2 kW to about 50 kW, such as from about 5 kW to about 20 kW, refining power per ton of the cellulose-rich solid phase. The mechanical refiner may transfer up to about 500 kW-hr refining energy per ton of the cellulose-rich solid phase, such as from about 50 kW-hr to about 200 kW-hr refining energy per ton of the cellulose-rich solid phase.

The process may utilize multiple mechanical refiners at different parts of the process. For example, between steps (c) and (d), at least a portion of the mixture may be conveyed to a second mechanical refiner, typically operated at the same or a lower refining pressure compared to that of the mechanical refiner in step (c). In certain embodiments, the first mechanical refiner in step (c) is a pressurized refiner and the second mechanical refiner is an atmospheric refiner.

In some embodiments, step (d) utilizes multiple enzymatic-hydrolysis reactors. For example, step (d) may utilize single-stage enzymatic hydrolysis configured for cellulose liquefaction and saccharification, wherein the single-stage enzymatic hydrolysis includes one or more tanks or vessels. Step (d) may utilize multiple-stage enzymatic hydrolysis configured for cellulose liquefaction followed by saccharification, wherein each stage includes one or more tanks or vessels. When multiple-stage enzymatic hydrolysis is employed, the process may include additional mechanical refining of the mixture, or a partially hydrolyzed form thereof, following at least a first stage of enzymatic hydrolysis.

The process according to some embodiments further includes:

introducing the mixture to a first enzymatic-hydrolysis reactor under effective hydrolysis conditions to produce a liquid hydrolysate comprising sugars from the refined cellulose-rich solids and optionally from the hemicellulose, and a residual cellulose-rich solid phase;

optionally separating at least some of the liquid hydrolysate from the residual cellulose-rich solid phase;

conveying the residual cellulose-rich solid phase through an additional mechanical refiner and/or recycling the residual cellulose-rich solid phase through the mechanical refiner, to generate refined residual cellulose-rich solids; and introducing the refined residual cellulose-rich solids to a second enzymatic-hydrolysis reactor under effective hydrolysis conditions, to produce additional sugars.

In some embodiments, a self-cleaning filter is configured downstream of the hydrolysis reactor to remove cellulosic fiber strands. The cellulosic fiber strands may be recycled back to the hydrolysis reactor.

Cellulase enzymes may be introduced directly to the mechanical refiner, so that simultaneous refining and hydrolysis occurs. Alternatively, or additionally, cellulase enzymes may be introduced to the cellulose-rich solid phase prior to step (c), so that during step (c), simultaneous refining and hydrolysis occurs. In these embodiments, the mechanical refiner is preferably operated at a maximum temperature of 75° C. or less to maintain effective hydrolysis conditions.

The process may include conversion of hemicellulose to the fermentation product, in various ways. For example, step (d) may include enzymatic hydrolysis of hemicellulose oligomers to generate fermentable monomer sugars. Step (e) may include enzymatic hydrolysis of hemicellulose oligomers to generate fermentable monomer sugars within the fermentor. The monomer sugars, derived from hemicellulose, may be co-fermented along with glucose or may be fermented in a second fermentor operated in series or parallel with the primary fermentor.

The process may further comprise removal of one or more fermentation inhibitors, such as by steam stripping. In some embodiments, acetic acid (a fermentation inhibitor) is removed and optionally recycled to the digestor.

The process typically includes concentrating the fermentation product by distillation. The distillation generates a distillation bottoms stream, and in some embodiments the distillation bottoms stream is evaporated in a distillation bottoms evaporator that is a mechanical vapor compression evaporator or is integrated in a multiple-effect evaporator train.

The fermentation product may be selected from the group consisting of ethanol, isopropanol, acetone, n-butanol, isobutanol, 1,4-butanediol, succinic acid, lactic acid, and combinations thereof. In certain embodiments, the fermentation product is ethanol (and $CO_2$ necessarily produced in fermentation).

Other variations of the invention provide a process to produce a fermentation product from lignocellulosic biomass, the process comprising:

(a) introducing a lignocellulosic biomass feedstock to a digestor, wherein the feedstock contains cellulose, hemicellulose, and lignin;

(b) exposing the feedstock to a reaction solution comprising steam or liquid hot water within the digestor, to solubilize at least a portion of the hemicellulose in a liquid phase and to provide a cellulose-rich solid phase;

(c) separating at least a portion of the liquid phase from the cellulose-rich solid phase;

(d) mechanically refining the cellulose-rich solid phase to reduce average particle size, thereby providing refined cellulose-rich solids;

(e) enzymatically hydrolyzing the refined cellulose-rich solids in a hydrolysis reactor with cellulase enzymes, to generate fermentable sugars;

(f) hydrolyzing the hemicellulose in the liquid phase, separately from step (e), to generate fermentable hemicellulose sugars; and (g) fermenting at least some of the fermentable sugars, and optionally at least some of the fermentable hemicellulose sugars, in a fermentor to produce a fermentation product.

Still other variations of the invention provide a process to produce a fermentation product from lignocellulosic biomass, the process comprising:

(a) introducing a lignocellulosic biomass feedstock to a digestor, wherein the feedstock contains cellulose, hemicellulose, and lignin;

(b) exposing the feedstock to a reaction solution comprising steam or liquid hot water within the digestor, to solubilize at least a portion of the hemicellulose in a liquid phase and to provide a cellulose-rich solid phase;

(c) mechanically refining the cellulose-rich solid phase to reduce average particle size, thereby providing refined cellulose-rich solids mixed with the liquid phase;

(d) separating at least a portion of the liquid phase from the refined cellulose-rich solids;

(e) enzymatically hydrolyzing the refined cellulose-rich solids in a hydrolysis reactor with cellulase enzymes, to generate fermentable sugars;

(f) hydrolyzing the hemicellulose in the liquid phase, separately from step (e), to generate fermentable hemicellulose sugars; and (g) fermenting at least some of the fermentable sugars, and optionally at least some of the fermentable hemicellulose sugars, in a fermentor to produce a fermentation product.

Yet other variations of the invention provide a process to produce fermentable sugars from lignocellulosic biomass, the process comprising:

(a) introducing a lignocellulosic biomass feedstock to a single-stage digestor, wherein the feedstock contains cellulose, hemicellulose, and lignin;

(b) exposing the feedstock to a reaction solution comprising steam or liquid hot water within the digestor, to solubilize at least a portion of the hemicellulose in a liquid phase and to provide a cellulose-rich solid phase;

(c) mechanically refining the cellulose-rich solid phase, together with the liquid phase, to reduce average particle size of the cellulose-rich solid phase, thereby providing a mixture comprising refined cellulose-rich solids and the liquid phase;

(d) enzymatically hydrolyzing the mixture in a hydrolysis reactor with cellulase enzymes, to generate fermentable sugars from the mixture; and (e) recovering or further treating the fermentable sugars.

DETAILED DESCRIPTION OF EMBODIMENTS OF THE INVENTION

Figure 1:
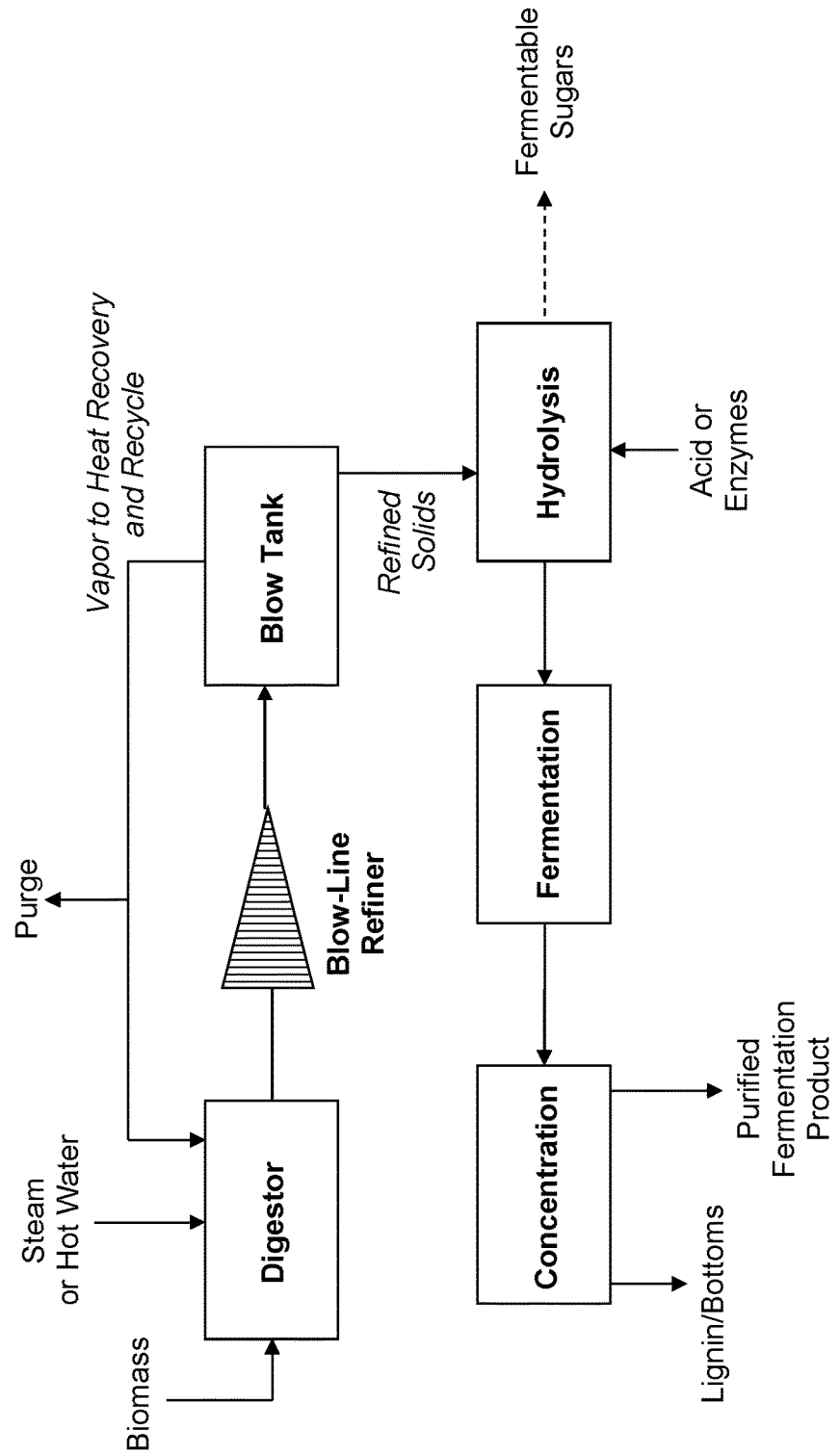
FIG. 1 is a simplified block-flow diagram depicting the process of some embodiments of the present invention, employing a pressurized blow-line refiner.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Some variations are premised on the discovery of a simple process for converting lignocellulosic biomass into fermentable sugars. In some embodiments, biomass is subjected to a steam or hot-water soak to dissolve hemicelluloses, with or without acetic acid addition. This step may optionally be followed by mechanical refining, such as in a hot-blow refiner, of the cellulose-rich (and lignin-rich) solids. The refined solids are then enzymatically hydrolyzed to generate sugars, in one or more hydrolysis (or liquefaction) reactors or vessels. An evaporation step following enzymatic hydrolysis, and prior to fermentation, may be included to remove water and potentially fermentation inhibitors from the hydrolysate. This intermediate evaporation reduces capital and operating costs of a process for cellulosic biofuels, such as ethanol and butanol.

Cellulose accessibility to cellulase enzymes is achieved according to the disclosed processes. The accessibility is maximized by using two controls that are (i) hydrothermal and (ii) mechanical in nature. Optimum hydrothermal conditions provide release of hemicelluloses from the biomass solid structure, which increases cellulose accessibility to enzymes, even when the lignin content remains high. Optimum mechanical refining conditions provide enhanced cellulose accessibility to enzymes.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only. Similarly, unit operations may be configured in different sequences, some units may be omitted, and other units may be added.

Figure 2:
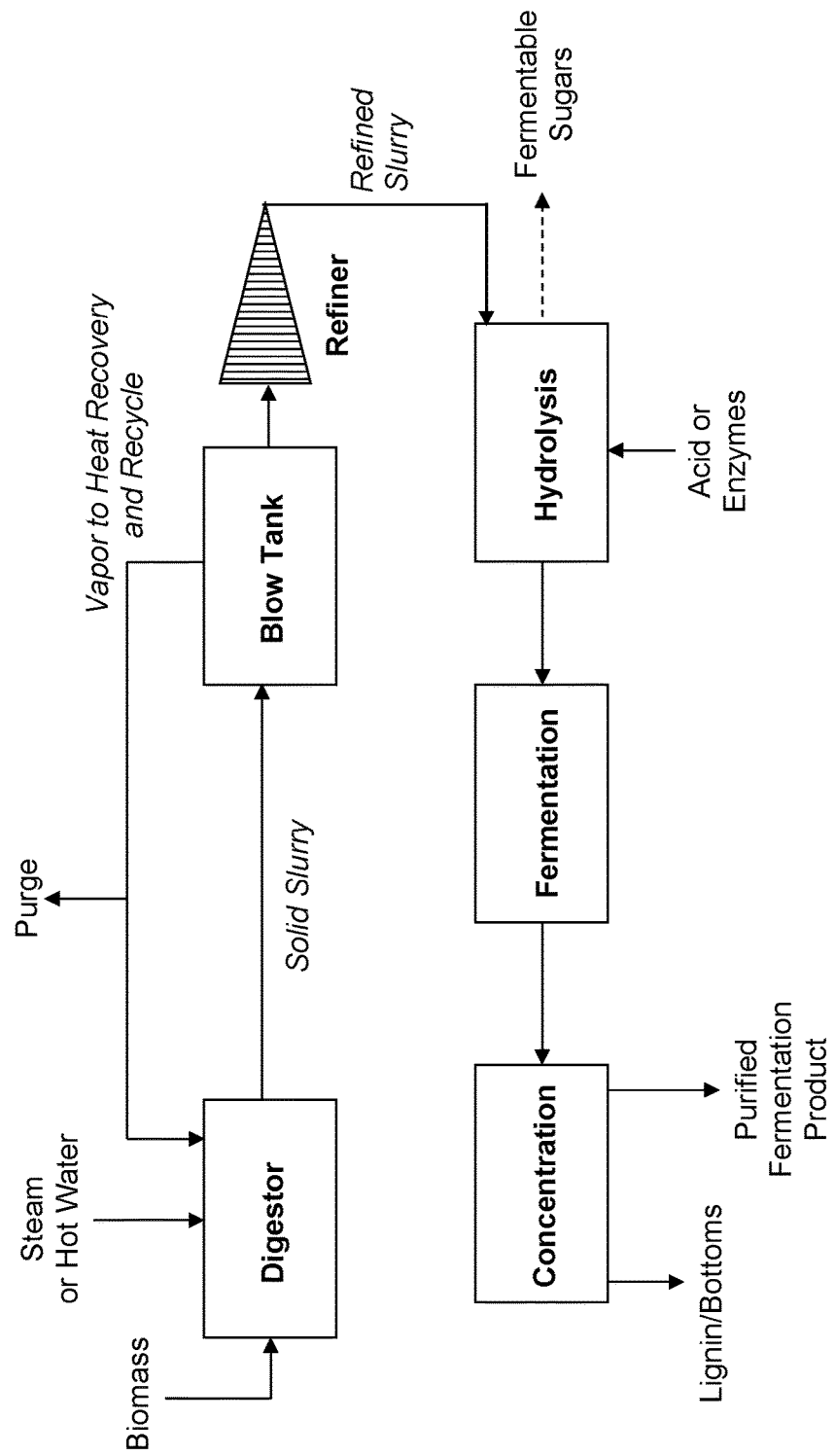
FIG. 2 is a simplified block-flow diagram depicting the process of some embodiments of the present invention, employing an atmospheric refiner.
Figure 3:
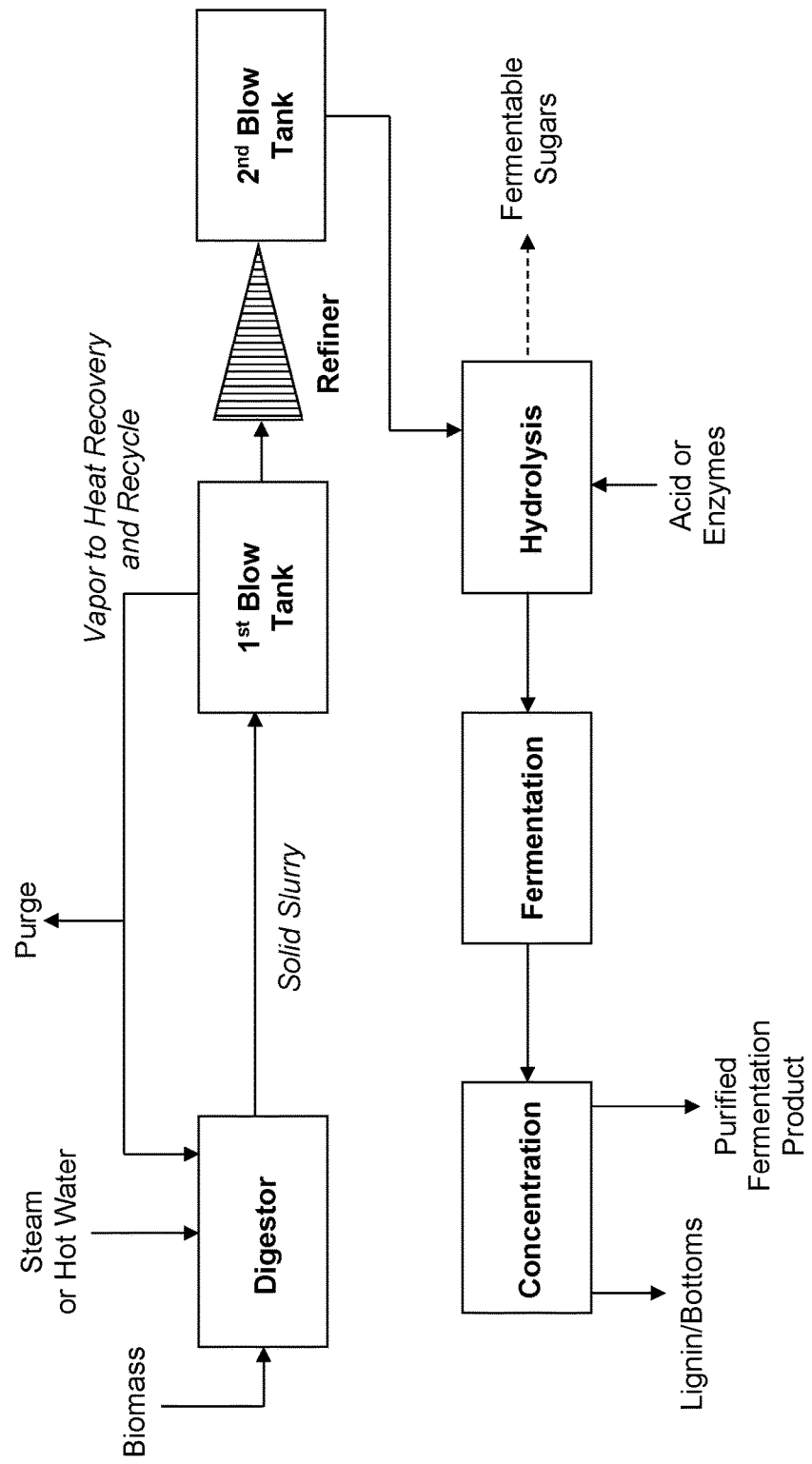
FIG. 3 is a simplified block-flow diagram depicting the process of some embodiments of the present invention, employing multiple blow tanks with a pressurized refiner between the blow tanks.
Figure 4:
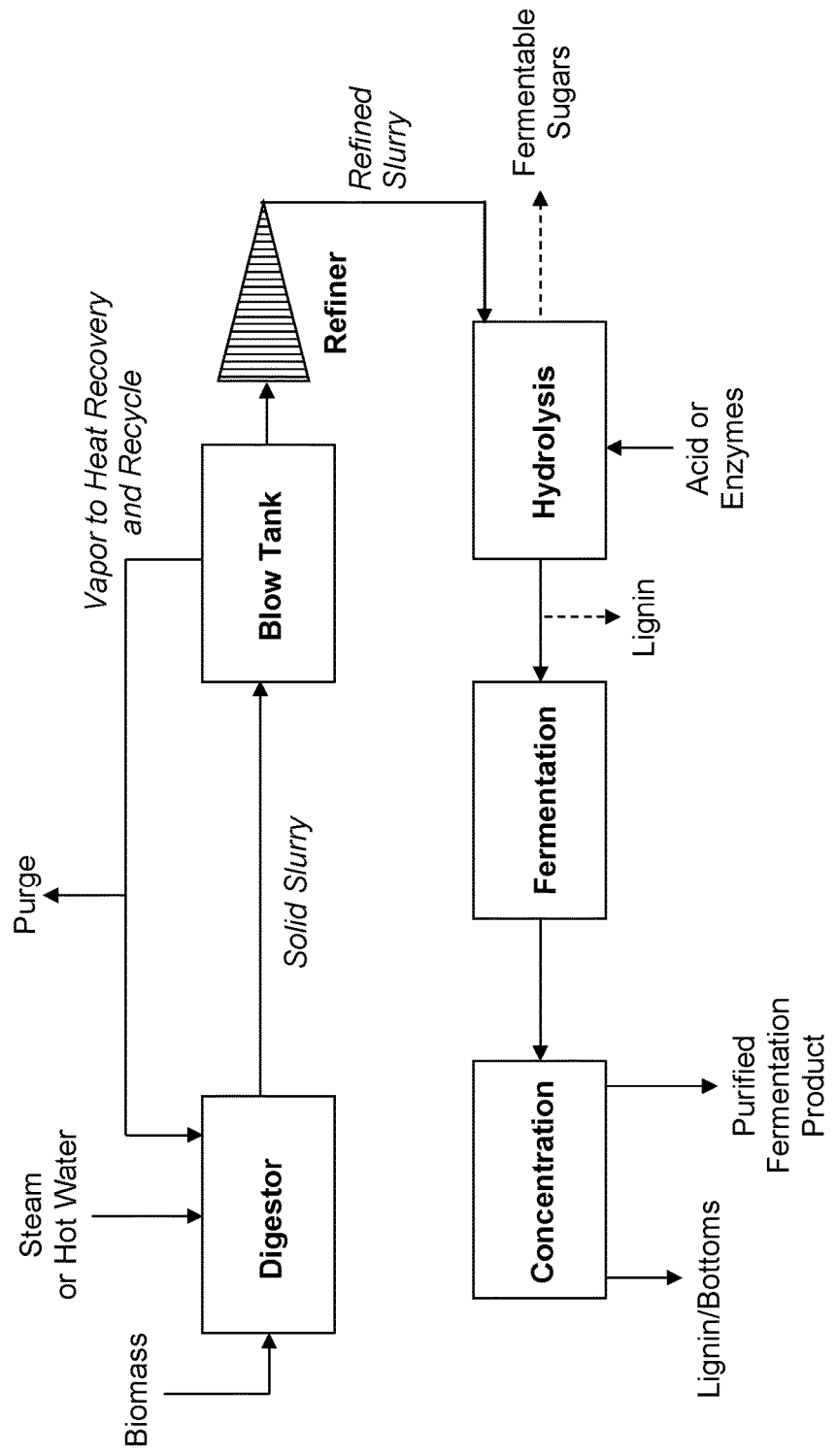
FIG. 4 is a simplified block-flow diagram depicting the process of some embodiments of the present invention, employing an atmospheric refiner and lignin recovery.
Figure 5:
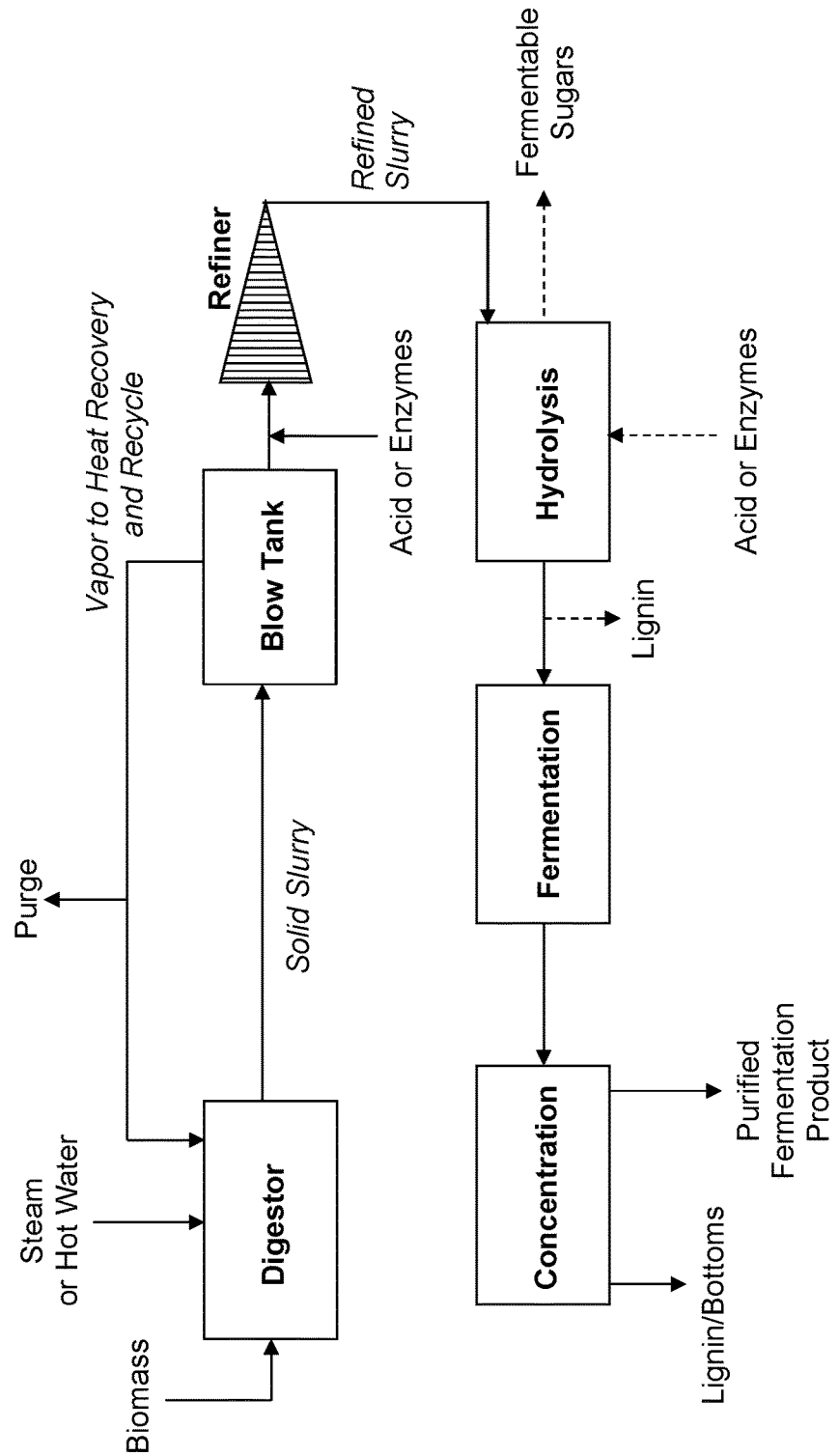
FIG. 5 is a simplified block-flow diagram depicting the process of some embodiments of the present invention, employing an atmospheric refiner and integrated enzymatic or acid hydrolysis.
Figure 6:
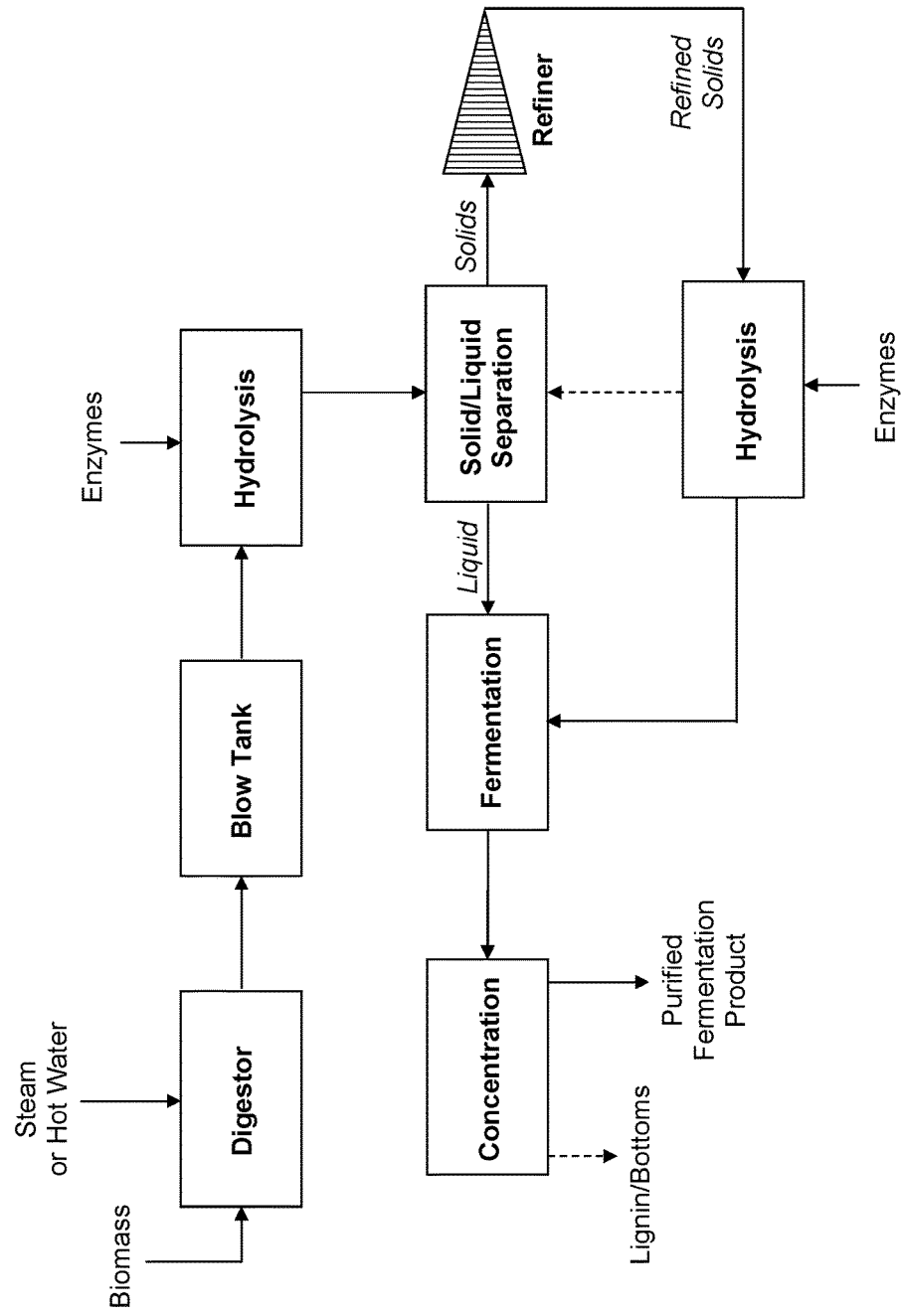
FIG. 6 is a simplified block-flow diagram depicting the process of some embodiments of the present invention, employing an atmospheric refiner and recycle of unconverted solids after enzymatic hydrolysis back to the refiner.
Figure 7:
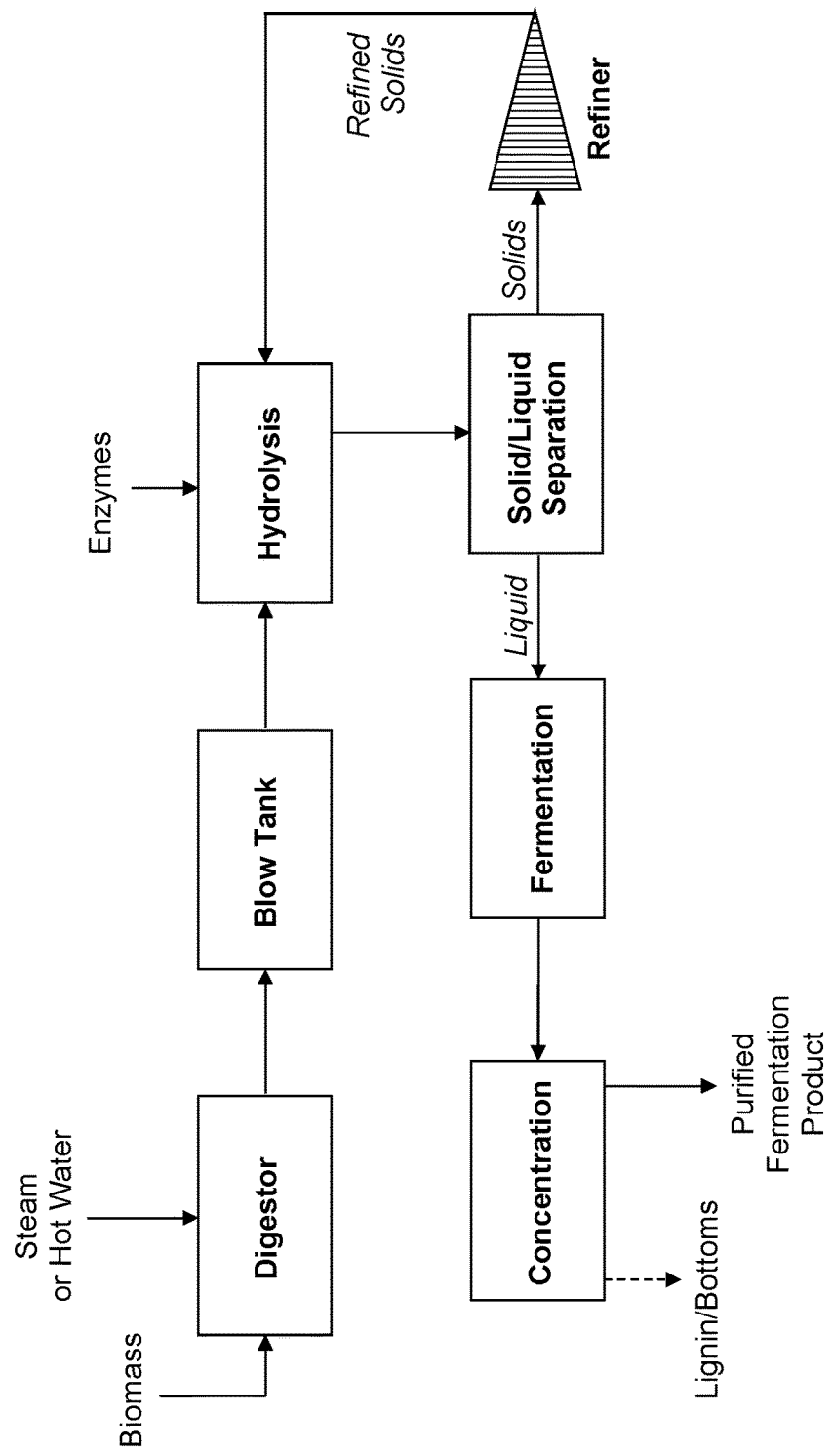
FIG. 7 is a simplified block-flow diagram depicting the process of some embodiments of the present invention, employing an atmospheric refiner and recycle of unconverted solids after solid-liquid separation back to the refiner.
Figure 8:
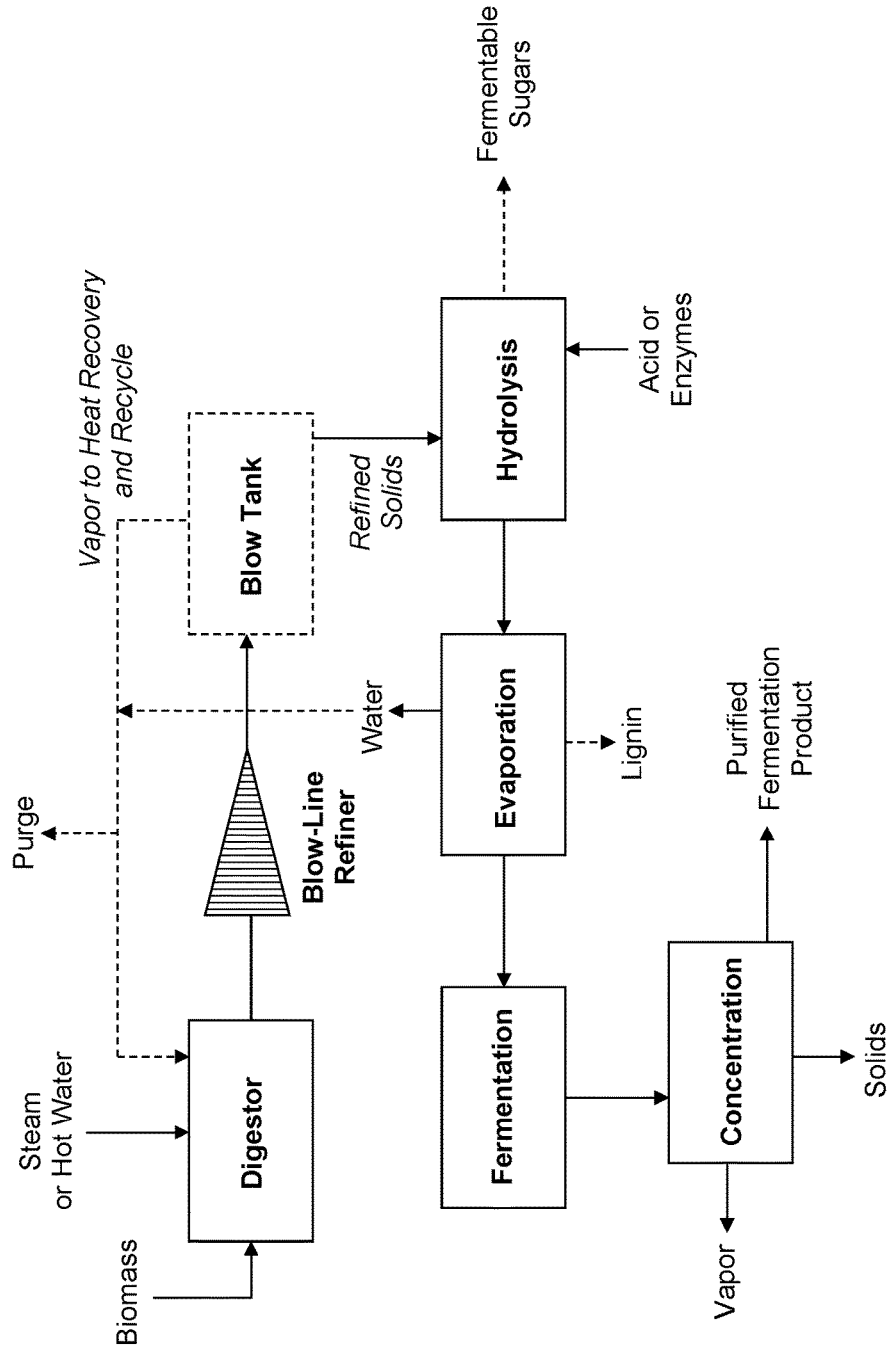
FIG. 8 is a simplified block-flow diagram depicting the integrated process of some embodiments of the present invention, with a pressurized refiner, intermediate hydrolysate evaporation, and concentration of the fermentation product.
Figure 9:
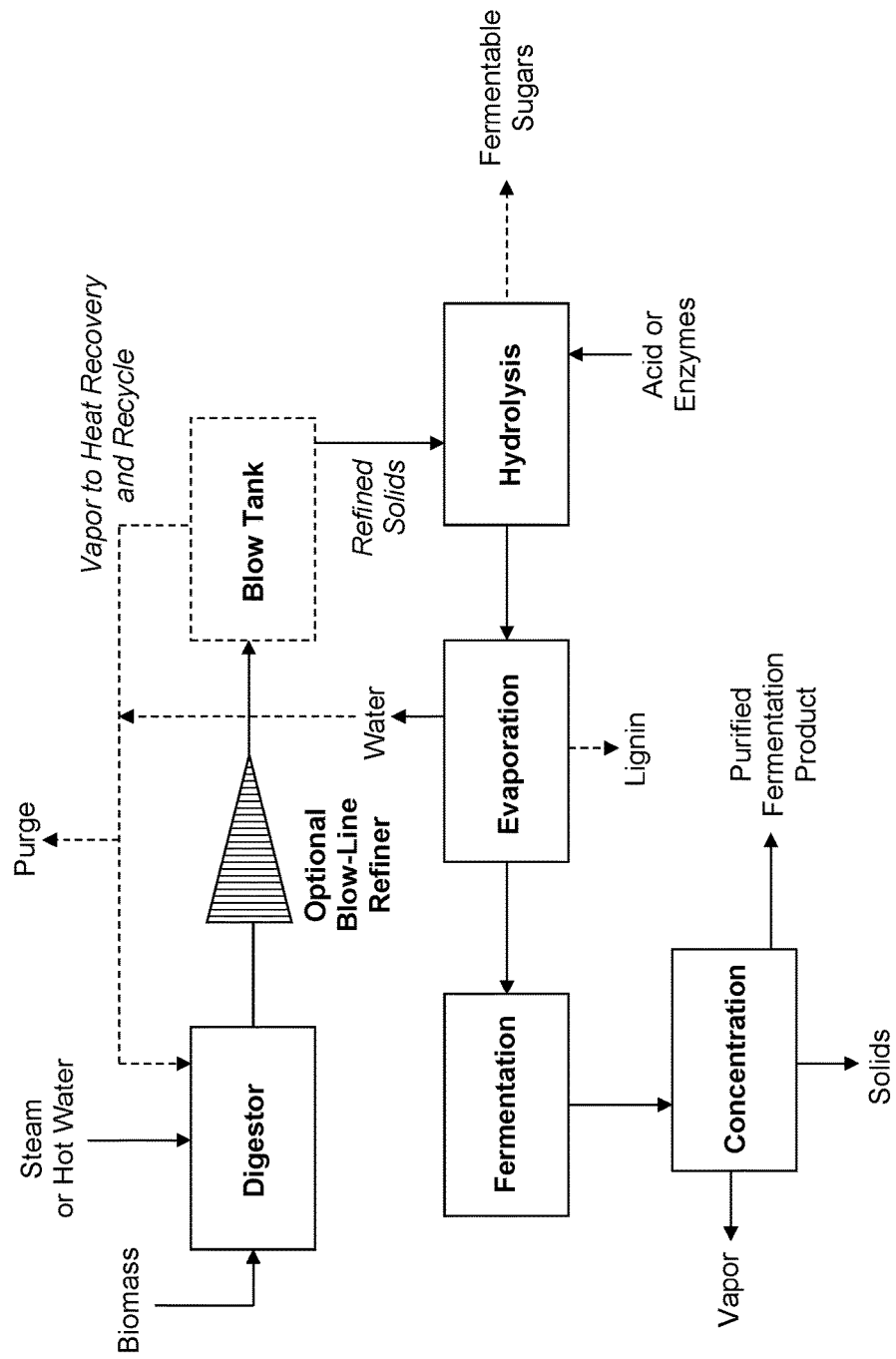
FIG. 9 is a simplified block-flow diagram depicting the integrated process of some embodiments of the present invention, with an optional mechanical refiner, intermediate hydrolysate evaporation, and concentration of the fermentation product.
Figure 10:
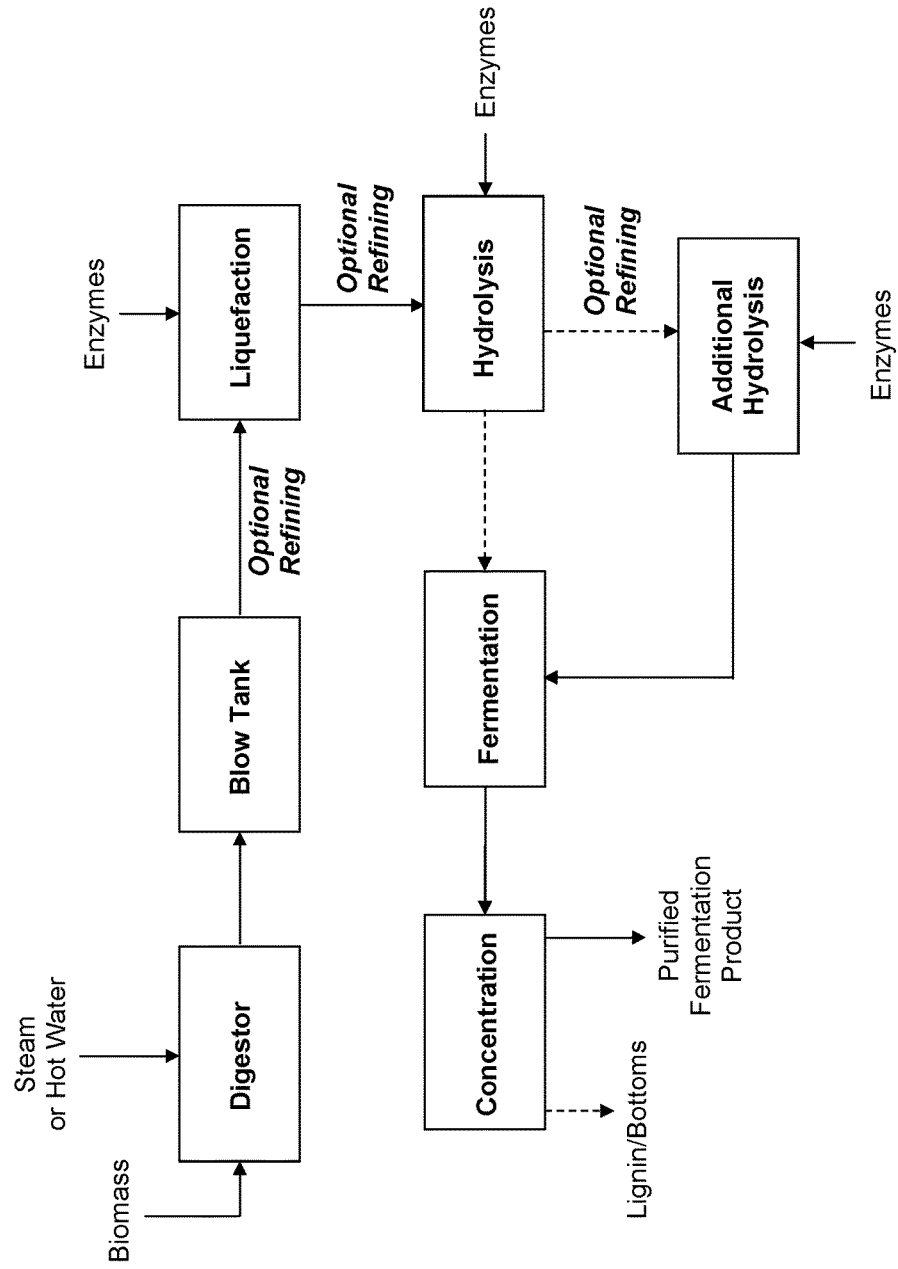
FIG. 10 is a simplified block-flow diagram depicting the process of some embodiments, employing additional refining and additional hydrolysis steps.

FIGS. 1 to 10 present simplified block-flow diagrams depicting the process of some embodiments of the present invention. The process of FIG. 1 employs a pressurized blow-line refiner. The process of employs an atmospheric refiner. The process of FIG. 3 employs multiple blow tanks with a pressurized refiner between the blow tanks. The process of FIG. 4 employs an atmospheric refiner and lignin recovery. The process of FIG. 5 employs an atmospheric refiner and integrated enzymatic or acid hydrolysis. The process of FIG. 6 employs an atmospheric refiner and recycle of unconverted solids after enzymatic hydrolysis back to the refiner. The process of FIG. 7 employs an atmospheric refiner and recycle of unconverted solids after solid-liquid separation back to the refiner. The process of FIG. 8 employs a pressurized refiner, intermediate hydrolysate evaporation, and concentration of the fermentation product. The process of FIG. 9 includes an optional mechanical refiner, intermediate hydrolysate evaporation, and concentration of the fermentation product. The process of FIG. 10 employs (optionally) several additional refining and additional hydrolysis steps.

Some variations provide a process to produce a fermentation product (e.g., ethanol) from lignocellulosic biomass, the process comprising:

(a) introducing a lignocellulosic biomass feedstock to a single-stage digestor, wherein the feedstock contains cellulose, hemicellulose, and lignin;

(b) exposing the feedstock to a reaction solution comprising steam or liquid hot water within the digestor, to solubilize at least a portion of the hemicellulose in a liquid phase and to provide a cellulose-rich solid phase;

(c) refining the cellulose-rich solid phase, together with the liquid phase, in a mechanical refiner to reduce average particle size of the cellulose-rich solid phase, thereby providing a mixture comprising refined cellulose-rich solids and the liquid phase;

(d) enzymatically hydrolyzing the mixture in a hydrolysis reactor with cellulase enzymes, to generate fermentable sugars from the mixture, wherein the hydrolysis reactor includes one or more hydrolysis stages; and (e) fermenting at least some of the fermentable sugars in a fermentor to produce a fermentation product.

In some embodiments, the lignocellulosic biomass feedstock is selected from the group consisting of hardwoods, softwoods, sugarcane bagasse, sugarcane straw, energy cane, corn stover, corn cobs, corn fiber, and combinations thereof.

The biomass feedstock may be selected from hardwoods, softwoods, forest residues, agricultural residues (such as sugarcane bagasse), industrial wastes, consumer wastes, or combinations thereof. In any of these processes, the feedstock may include sucrose. In some embodiments with sucrose present in the feedstock (e.g., sugarcane or sugar beets), a majority of the sucrose is recovered as part of the fermentable sugars. In some embodiments with dextrose (or starch that is readily hydrolyzed to dextrose) present in the feedstock (e.g., corn), the dextrose is recovered as part of the fermentable sugars.

Some embodiments of the invention enable processing of "agricultural residues," which for present purposes is meant to include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, *miscanthus*, energy cane, or combinations thereof.

The lignocellulosic biomass feedstock may be pretreated, prior to step (a), using one or more techniques selected from the group consisting of cleaning, washing, presteaming, drying, milling, particle size-classifying, and combinations thereof. The process may include cleaning the starting feedstock by wet or dry cleaning. The process may include size reduction, hot-water soaking, dewatering, steaming, or other operations, upstream of the digestor.

In some embodiments, the reaction solution further comprises an acid, such as (but not limited to) acetic acid. In some embodiments, at least a portion of the reaction solution is introduced to the feedstock in a pre-impregnator prior to step (b).

Step (b) may include a digestor residence time from about 2 minutes to about 4 hours. In some embodiments, the digestor residence time is about 10 minutes or less. In various embodiments, the digestor residence time is about 15, 20, 25, 30, 35, 40, 45, 50, 55 minutes, or about 1.0, 1.5, 2.0, 2.5, 3.0, 3.5, or 4.0 hours.

Step (b) may include a digestor temperature from about 150° C. to about 220° C., such as from about 180° C. to about 200° C. In various embodiments, the digestor temperature is about 160° C., 165° C., 170° C., 175° C., 180° C., 181° C., 182° C., 183° C., 184° C., 185° C., 186° C., 187° C., 188° C., 189° C., 190° C., 195° C., or 200° C. At a given reaction severity, there is a trade-off between time and temperature. Optionally, a temperature profile is specified for the digestor.

It is noted that the digestor temperature may be measured in a variety of ways. The digestor temperature may be taken as the vapor temperature within the digestor. The digestor temperature may be measured from the temperature of the solids and/or the liquids (or a reacting mixture thereof). The digestor temperature may be taken as the digestor inlet temperature, the digestor outlet temperature, or a combination or correlation thereof. The digestor temperature may be measured as, or correlated with, the digestor wall temperature. Note that especially at short residence times (e.g., 5 minutes), the temperatures of different phases present vapor, liquid, solid, and metal walls) may not reach equilibrium.

Step (b) may include a digestor pressure from atmospheric pressure up to about 40 bar, such as from about 10 bar to about 20 bar. The digestor pressure may correspond to the steam saturation pressure at the digestor temperature. In some embodiments, the digestor pressure is higher than the steam saturation pressure at the digestor temperature, such as when supersaturated water vapor is desired, or when an inert gas is also present in the digestor. In some embodiments, the digestor pressure is lower than the steam saturation pressure at the digestor temperature, such as when superheated steam is desired, or when a digestor vapor bleed line is present.

Step (b) may be conducted at a digestor liquid-solid weight ratio from about 0.1 to about 10, such as from about 1 to about 4, preferably about 2 or less. In various embodiments, the digestor liquid-solid weight ratio is about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0.

Step (b) may be conducted at a digestor pH from about 2 to about 6, such as from about 3 to 5, or from about 3.5 to about 4.5. In various embodiments, the digestor pH is about 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, or 4.9. Generally, a lower pH gives a higher reaction severity. Typically, the digestor pH is not controlled but is dictated by the composition of the starting feedstock (e.g., acid content or buffer capacity) and whether an acid is included in the aqueous reaction solution. Based on measurements made to the starting material or dynamic measurements made or correlated during the process, an additive (e.g., an acid or base) may be added to the digestor to vary the digestor pH.

In some embodiments of the process, a blow tank is configured for receiving the cellulose-rich solid phase or the refined cellulose-rich solids at a pressure lower than the digestor pressure. The blow tank may be disposed downstream of the digestor and upstream of the mechanical refiner, i.e. between the digestor and refiner. Or the blow tank may be disposed downstream of the mechanical refiner. In certain embodiments, a first blow tank is disposed upstream of the mechanical refiner and a second blow tank is disposed downstream of the mechanical refiner. Optionally, vapor is separated from the blow tank(s). The vapor may be purged and/or condensed or compressed and returned to the digestor. In either case, heat may be recovered from at least some of the vapor.

The mechanical refiner may be selected from the group consisting of a hot-blow refiner, a hot-stock refiner, a blow-line refiner, a disk refiner, a conical refiner, a cylindrical refiner, an in-line defibrator, an extruder, a homogenizer, and combinations thereof.

The mechanical refiner may be operated at a refining pressure selected from about 1 bar to about 20 bar. In some embodiments, the refining pressure is about 3 bar or less. In some embodiment, the mechanical refiner is operated at or about at atmospheric pressure.

The mechanical refiner may operate at an electrical load from about 2 kW to about 50 kW, such as from about 5 kW to about 20 kW, refining power per ton of the cellulose-rich solid phase. In various embodiments, the mechanical refiner operates at an electrical load of about 3, 4, 5, 6, 7, 8, 9, 10, 11, 12, 13, 14, 15, 16, 17, 18, 19, 20, 25, 30, 35, or 40 kW refining power per ton of the cellulose-rich solid phase.

The mechanical refiner may transfer up to about 500 kW-hr refining energy per ton of the cellulose-rich solid phase, such as from about 50 kW-hr to about 200 kW-hr refining energy per ton of the cellulose-rich solid phase. In various embodiments, the mechanical refiner transfers about 10, 20, 30, 40, 50, 60, 70, 80, 90, 100, 110, 120, 130, 140, 150, 160, 170, 180, 190, 200, 225, 250, 275, 300, 325, 350, or 400 kW-hr refining energy per ton of the cellulose-rich solid phase.

The mechanical refiner may be designed and operating using principles that are well-known in the art of pulp and paper plants and biorefineries. For example, refiner plate gap dimensions may be varied, such as from about 0.1 mm to about 10 mm, or about 0.5 mm to about 2 mm, to reach the desired particle-size distribution. The choice of gap dimensions may depend on the nature of the starting feedstock, for example.

In some embodiments, the mechanical refiner is designed and/or adjusted to achieve certain average fiber lengths, such as about 1 mm, 0.9 mm, 0.8 mm, 0.7 mm, 0.6 mm, 0.5 mm, 0.4 mm, 0.3 mm, 0.2 mm, 0.1 mm or less. Generally speaking, shorter fibers or fibers with lower diameter are easier to enzymatically hydrolyze to sugars, compared to larger fibers.

In some embodiments, the mechanical refiner is designed and/or adjusted to achieve a certain shives (bundles of fibers) content, such as less than about 5%, 4%, 3%, 2%, 1%, 0.5%, or less. Shives are not desirable because they tend to be more difficult to enzymatically hydrolyze to sugars. Knots and other large particles should be refined as well.

The process may utilize multiple mechanical refiners at different parts of the process. For example, between steps (c) and (d), at least a portion of the mixture may be conveyed to a second mechanical refiner, typically operated at the same or a lower refining pressure compared to that of the mechanical refiner in step (c). In certain embodiments, the first mechanical refiner in step (c) is a pressurized refiner and the second mechanical refiner is an atmospheric refiner.

In some embodiments, step (d) utilizes multiple enzymatic-hydrolysis reactors. For example, step (d) may utilize single-stage enzymatic hydrolysis configured for cellulose liquefaction and saccharification, wherein the single-stage enzymatic hydrolysis includes one or more tanks or vessels. Step (d) may utilize multiple-stage enzymatic hydrolysis configured for cellulose liquefaction followed by saccharification, wherein each stage includes one or more tanks or vessels. When multiple-stage enzymatic hydrolysis is employed, the process may include additional mechanical refining of the mixture, or a partially hydrolyzed form thereof, following at least a first stage of enzymatic hydrolysis.

In some embodiments, non-acid and non-enzyme catalysts may be employed for co-hydrolyzing glucose oligomers and hemicellulose oligomers. For example, base catalysts, solid catalysts, ionic liquids, or other effective materials may be employed.

The process according to some embodiments further includes:

introducing the mixture to a first enzymatic-hydrolysis reactor under effective hydrolysis conditions to produce a liquid hydrolysate comprising sugars from the refined cellulose-rich solids and optionally from the hemicellulose, and a residual cellulose-rich solid phase;

optionally separating at least some of the liquid hydrolysate from the residual cellulose-rich solid phase;

conveying the residual cellulose-rich solid phase through an additional mechanical refiner and/or recycling the residual cellulose-rich solid phase through the mechanical refiner, to generate refined residual cellulose-rich solids; and introducing the refined residual cellulose-rich solids to a second enzymatic-hydrolysis reactor under effective hydrolysis conditions, to produce additional sugars.

In some embodiments, a self-cleaning filter is configured downstream of the hydrolysis reactor to remove cellulosic fiber strands. The cellulosic fiber strands may be recycled, at least in part, back to the hydrolysis reactor.

Cellulase enzymes may be introduced directly to the mechanical refiner, so that simultaneous refining and hydrolysis occurs. Alternatively, or additionally, cellulase enzymes may be introduced to the cellulose-rich solid phase prior to step (c), so that during step (c), simultaneous refining and hydrolysis occurs. In these embodiments, the mechanical refiner is preferably operated at a maximum temperature of 75° C., 70° C., 65° C., 60° C., 55° C., 50° C. or less to maintain effective hydrolysis conditions.

The process may include conversion of hemicellulose to the fermentation product, in various ways. For example, step (d) may include enzymatic hydrolysis of hemicellulose oligomers to generate fermentable monomer sugars. Step (e) may include enzymatic hydrolysis of hemicellulose oligomers to generate fermentable monomer sugars within the fermentor. The monomer sugars, derived from hemicellulose, may be co-fermented along with glucose or may be fermented in a second fermentor operated in series or parallel with the primary fermentor.

The process may further comprise removal of one or more fermentation inhibitors, such as by steam stripping. In some embodiments, acetic acid (a fermentation inhibitor) is removed and optionally recycled to the digestor.

The process typically includes concentrating the fermentation product by distillation. The distillation generates a distillation bottoms stream, and in some embodiments the distillation bottoms stream is evaporated in a distillation bottoms evaporator that is a mechanical vapor compression evaporator or is integrated in a multiple-effect evaporator train.

The fermentation product may be selected from the group consisting of ethanol, isopropanol, acetone, n-butanol, isobutanol, 1,4-butanediol, succinic acid, lactic acid, and combinations thereof. In certain embodiments, the fermentation product is ethanol (and $CO_2$ necessarily co-produced in fermentation).

The solid yield (also known as pulp yield or fiber yield) is the fraction of solids remaining (not dissolved) following digestion and refining, but prior to enzymatic hydrolysis, relative to the starting biomass feedstock. The solid yield of the process may vary, such as from about 60% to about 90%, typically from about 70% to about 80%. The solid yield does not include dissolved solids (e.g., hemicellulose sugars in solution). In various embodiments, the solid yield is about 70%, 71%, 72%, 73%, 74%, 75%, 76%, 77%, 78%, 79%, or 80%.

The sugar yield (also known as carbohydrate yield) is the fraction of sugar monomers and oligomers following enzymatic hydrolysis, but prior to fermentation of the hydrolysate, relative to the solid material entering hydrolysis from digestion and any refining. The sugar yield of the process may vary, such as from about 40% to about 80% (or more), preferably at least 50%. In various embodiments, the sugar yield is about 50%, 52%, 54%, 56%, 58%, 60%, 62%, 64%, 66%, 68%, 70%, or more.

The fraction of starting hemicellulose that is extracted into solution may be from about 50% to about 95%, such as about 55%, 60%, 65%, 70%, 75%, 80%, 85%, or 90%.

The fermentation product yield (e.g., ethanol yield) is the yield of final product produced in fermentation, relative to the theoretical yield if all sugars are fermented to the product. The theoretical fermentation yield accounts for any necessary co-products, such as carbon dioxide in the case of ethanol. In the case of ethanol, the ethanol yield of the process may vary, such as from about 65% to about 95%, typically at least 80%. In various embodiments, the ethanol yield is about 75%, 76%, 77%, 78%, 79%, 80%, 81%, 82%, 83%, 84%, 85%, 86%, 87%, 88%, 89%, 90% or more. An ethanol yield on the basis of starting feedstock can also be calculated. In various embodiments, the ethanol yield is from about 45 gal/T (T is dry tons of starting lignocellulosic feedstock) to about 85 gal/T, typically about 60 gal/T or more.

Other variations of the invention provide a process to produce a fermentation product from lignocellulosic biomass, the process comprising:

(a) introducing a lignocellulosic biomass feedstock to a digestor, wherein the feedstock contains cellulose, hemicellulose, and lignin;

(b) exposing the feedstock to a reaction solution comprising steam or liquid hot water within the digestor, to solubilize at least a portion of the hemicellulose in a liquid phase and to provide a cellulose-rich solid phase;

(c) separating at least a portion of the liquid phase from the cellulose-rich solid phase;

(d) mechanically refining the cellulose-rich solid phase to reduce average particle size, thereby providing refined cellulose-rich solids;

(e) enzymatically hydrolyzing the refined cellulose-rich solids in a hydrolysis reactor with cellulase enzymes, to generate fermentable sugars;

(f) hydrolyzing the hemicellulose in the liquid phase, separately from step (e), to generate fermentable hemicellulose sugars; and (g) fermenting at least some of the fermentable sugars, and optionally at least some of the fermentable hemicellulose sugars, in a fermentor to produce a fermentation product.

Still other variations of the invention provide a process to produce a fermentation product from lignocellulosic biomass, the process comprising:

(a) introducing a lignocellulosic biomass feedstock to a digestor, wherein the feedstock contains cellulose, hemicellulose, and lignin;

(b) exposing the feedstock to a reaction solution comprising steam or liquid hot water within the digestor, to solubilize at least a portion of the hemicellulose in a liquid phase and to provide a cellulose-rich solid phase;

(c) mechanically refining the cellulose-rich solid phase to reduce average particle size, thereby providing refined cellulose-rich solids mixed with the liquid phase;

(d) separating at least a portion of the liquid phase from the refined cellulose-rich solids;

(e) enzymatically hydrolyzing the refined cellulose-rich solids in a hydrolysis reactor with cellulase enzymes, to generate fermentable sugars;

(f) hydrolyzing the hemicellulose in the liquid phase, separately from step (e), to generate fermentable hemicellulose sugars; and (g) fermenting at least some of the fermentable sugars, and optionally at least some of the fermentable hemicellulose sugars, in a fermentor to produce a fermentation product.

Yet other variations of the invention provide a process to produce fermentable sugars from lignocellulosic biomass, the process comprising:

(a) introducing a lignocellulosic biomass feedstock to a single-stage digestor, wherein the feedstock contains cellulose, hemicellulose, and lignin;

(b) exposing the feedstock to a reaction solution comprising steam or liquid hot water within the digestor, to solubilize at least a portion of the hemicellulose in a liquid phase and to provide a cellulose-rich solid phase;

(c) mechanically refining the cellulose-rich solid phase, together with the liquid phase, to reduce average particle size of the cellulose-rich solid phase, thereby providing a mixture comprising refined cellulose-rich solids and the liquid phase;

(d) enzymatically hydrolyzing the mixture in a hydrolysis reactor with cellulase enzymes, to generate fermentable sugars from the mixture; and (e) recovering or further treating the fermentable sugars.

In some variations, a process is provided for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) conveying the digested stream through a mechanical refiner, thereby generating a refined stream with reduced average particle size of the cellulose-rich solids;

(d) separating a vapor from the refined stream;

(e) introducing the refined stream to an enzymatic hydrolysis unit under effective hydrolysis conditions to produce sugars from the cellulose-rich solids and optionally from the hemicellulose oligomers; and (f) recovering or further processing at least some of the sugars as fermentable sugars.

Some variations provide a process for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) conveying the digested stream through a mechanical refiner, thereby generating a refined stream with reduced average particle size of the cellulose-rich solids;

(d) separating a vapor from the refined stream;

(e) introducing the refined stream to an acid hydrolysis unit under effective hydrolysis conditions to produce sugars from the cellulose-rich solids and optionally from the hemicellulose oligomers;

(f) recovering or further processing at least some of the sugars as fermentable sugars.

Certain embodiments provide a process for producing ethanol from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) conveying the digested stream through a blow-line refiner, thereby generating a refined stream with reduced average particle size of the cellulose-rich solids;

(d) separating a vapor from the refined stream;

(e) introducing the refined stream to an enzymatic hydrolysis unit under effective hydrolysis conditions to produce sugars from the cellulose-rich solids and from the hemicellulose oligomers;

(f) fermenting the sugars to produce ethanol in dilute solution; and (g) concentrating the dilute solution to produce an ethanol product.

In some variations, a process for producing fermentable sugars from cellulosic biomass comprises:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) reducing pressure of the digested stream;

(d) introducing the digested stream to an enzymatic hydrolysis unit under effective hydrolysis conditions to produce a liquid phase comprising sugars from the cellulose-rich solids and optionally from the hemicellulose oligomers, and a solid phase comprising the cellulose-rich solids;

(e) separating the liquid phase and the solid phase from step (d);

(f) conveying the solid phase through a mechanical refiner, thereby generating a refined stream with reduced average particle size of the cellulose-rich solids;

(g) recycling the refined stream to the enzymatic hydrolysis unit, to produce additional sugars from the cellulose-rich solids contained in the solid phase from step (d); and (h) recovering or further processing at least some of the sugars and at least some of the additional sugars as fermentable sugars.

Other variations provide a process for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) reducing pressure of the digested stream;

(d) introducing the digested stream to a first enzymatic hydrolysis unit under effective hydrolysis conditions to produce a liquid phase comprising sugars from the cellulose-rich solids and optionally from the hemicellulose oligomers, and a solid phase comprising the cellulose-rich solids;

(e) separating the liquid phase and the solid phase from step (d);

(f) conveying the solid phase through a mechanical refiner, thereby generating a refined stream with reduced average particle size of the cellulose-rich solids;

(g) recycling the refined stream to a second enzymatic hydrolysis unit, to produce additional sugars from the cellulose-rich solids contained in the solid phase from step (d); and (h) recovering or further processing at least some of the sugars and/or the additional sugars as fermentable sugars.

Other variations provide a process for producing a fermentation product from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) optionally exploding the digested stream, thereby generating an exploded stream with reduced average particle size of the cellulose-rich solids;

(d) introducing the digested stream and/or (if step (c) is conducted) the exploded stream to an enzymatic hydrolysis unit under effective hydrolysis conditions to produce a sugar-containing hydrolysate;

(e) evaporating the hydrolysate using a multiple-effect evaporator or a mechanical vapor compression evaporator, to produce a concentrated hydrolysate;

(f) fermenting the concentrated hydrolysate to produce a dilute fermentation product; and (g) concentrating the dilute fermentation product to produce a concentrated fermentation product.

Some variations provide a process for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) optionally conveying the digested stream through a mechanical refiner, thereby generating a refined stream with reduced average particle size of the cellulose-rich solids;

(d) introducing the digested stream and/or (if step (c) is conducted) the refined stream to an enzymatic hydrolysis unit under effective hydrolysis conditions to produce a sugar-containing hydrolysate;

(e) optionally evaporating the hydrolysate using a multiple-effect evaporator or a mechanical vapor compression evaporator, to produce a concentrated hydrolysate;

(f) fermenting the hydrolysate to produce a dilute fermentation product; and (g) concentrating the dilute fermentation product to produce a concentrated fermentation product.

Other variations provide a process for producing a fermentation product from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) optionally exploding the digested stream, thereby generating an exploded stream with reduced average particle size of the cellulose-rich solids;

(d) introducing the digested stream and/or (if step (c) is conducted) the exploded stream to an enzymatic hydrolysis unit under effective hydrolysis conditions to produce a sugar-containing hydrolysate;

(e) evaporating the hydrolysate using a multiple-effect evaporator or a mechanical vapor compression evaporator, to produce a concentrated hydrolysate;

(f) fermenting the concentrated hydrolysate to produce a dilute fermentation product; and (g) concentrating the dilute fermentation product to produce a concentrated fermentation product.

Other variations provide a process for producing a fermentation product from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) optionally conveying at least a portion of the digested stream through a first mechanical refiner in a blow line;

(d) optionally conveying at least a portion of the digested stream through a second mechanical refiner following pressure reduction of the digested stream;

(e) introducing the digested stream and/or (if step (c) and/or step (d) is conducted) a mechanically treated derivative thereof, to an enzymatic liquefaction unit under effective liquefaction conditions to produce a first intermediate stream;

(f) optionally conveying at least a portion of the first intermediate stream through a third mechanical refiner;

(g) introducing the first intermediate stream and/or (if step (f) is conducted) a mechanically treated derivative thereof, to a first enzymatic hydrolysis unit under effective hydrolysis conditions to produce a second intermediate stream;

(h) optionally conveying at least a portion of the second intermediate stream through a fourth mechanical refiner;

(i) introducing the second intermediate stream and/or (if step (h) is conducted) a mechanically treated derivative thereof, to a second enzymatic hydrolysis unit under effective hydrolysis conditions to produce a concentrated hydrolysate;

(j) fermenting the concentrated hydrolysate to produce a dilute fermentation product; and (k) concentrating the dilute fermentation product to produce a concentrated fermentation product.

The process may include no refiner, or only the first mechanical refiner, or only the second mechanical refiner, or only the third mechanical refiner, or only the fourth mechanical refiner, or any combination thereof (e.g., any two of such refiners, or any three of such refiners, or all four of such refiners).

Some variations provide a process for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) optionally conveying the digested stream through a mechanical refiner, thereby generating a refined stream with reduced average particle size of the cellulose-rich solids;

(d) introducing the digested stream and/or (if step (c) is conducted) the refined stream to an enzymatic hydrolysis unit under effective hydrolysis conditions to produce a sugar-containing hydrolysate;

(e) evaporating the hydrolysate using a multiple-effect evaporator or a mechanical vapor compression evaporator, to produce a concentrated hydrolysate;

(f) fermenting the concentrated hydrolysate to produce a dilute fermentation product; and (g) concentrating the dilute fermentation product to produce a concentrated fermentation product.

Other variations of the invention provide a process for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) conveying the digested stream through a mechanical refiner, thereby generating a refined stream with reduced average particle size of the cellulose-rich solids;

(d) introducing enzymes to the mechanical refiner and maintaining effective hydrolysis conditions to produce sugars from the cellulose-rich solids and optionally from the hemicellulose oligomers, simultaneously with step (c);

(e) evaporating water from the hydrolysate from step (d); and (f) recovering or further processing at least some of the sugars as fermentable sugars.

Some variations provide a process for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) conveying the digested stream through a mechanical refiner, thereby generating a refined stream with reduced average particle size of the cellulose-rich solids;

(d) introducing the refined stream to an acid hydrolysis unit under effective hydrolysis conditions to produce sugars from the cellulose-rich solids and optionally from the hemicellulose oligomers;

(e) separating a vapor from the refined stream before, during, or after step (d); and (f) recovering or further processing at least some of the sugars as fermentable sugars.

In some embodiments, the reaction solution comprises or consists essentially of steam in saturated, superheated, or supersaturated form. In these or other embodiments, the reaction solution comprises or consists essentially of pressurized liquid hot water.

In certain embodiments, a combination of steam and liquid hot water is employed. For example, a pre-steaming step may be employed prior to the digestor, and then liquid hot water may be introduced to the digestor along with pre-steamed biomass. Depending on the temperature and pressure, the steam may partially or completely condense, or the liquid hot water may partially or completely enter the vapor phase, in the digestor head space and/or within open space between cellulose fibers, for example.

The reaction solution optionally includes an acid catalyst, to assist in extraction of hemicelluloses from the starting material, and possibly to catalyze some hydrolysis. In some embodiments, the acid is a sulfur-containing acid (e.g., sulfur dioxide). In some embodiments, the acid is acetic acid, which may be recovered from the digested stream (i.e., from downstream operations). Additives may be present in the reaction solution, such as acid or base catalysts, or other compounds present in recycled streams.

Many types of digestors are possible. The digestor may be horizontal, vertical, or inclined. The digestor may or may not have any internal agitator or means for agitation. The digestor may be fixed in place, or be allowed to rotate (e.g., about its axial or radial dimensions). The digestor may be operated in upflow or downflow mode, relative to the solids or the solid-liquid mixture. When there is excess liquid, the digestor may be operated either cocurrently or countercurrently (solid flow versus liquid flow). The digestor may be operated continuously, semi-continuously, in batch, or some combination or hybrid thereof. The flow pattern in the digestor may be plug flow, well-mixed, or any other flow pattern. The digestor may be heated internally or externally, such as by steam, hot oil, etc. Generally, the principles of chemical-reactor engineering may be applied to digestor design and operation.

In certain preferred embodiments of the invention, the digestor is a vertical digestor. In some embodiments, the digestor is not or does not include a horizontal digestor (e.g., Pandia-type). Although the prior art tends to teach away from a vertical digestor for processing annual fibers (agricultural residues), it has been discovered that a single-stage pretreatment in a vertical digestor works surprisingly well for steam or hot-water extraction of agricultural residues prior to enzymatic hydrolysis.

As intended herein, a "vertical digestor" can include non-vertical ancillary equipment, including feeding and discharge equipment. For example, a horizontal or inclined inlet (e.g., plug-screw feeder) or horizontal or inclined outlet (e.g., plug-screw discharger), a horizontal or inclined pre-impregnator, a horizontal or inclined blow line, and so on may be included in the process when a vertical digestor is utilized. Also, a vertical digestor may be substantially vertical but may contain sections or zones that are not strictly vertical, and may contain side-streams (inlet or outlet), internal recycle streams, and so on that may be construed as non-vertical. In some embodiments, a vertical digestor has a varying diameter along its length (height).

In certain preferred embodiments of the invention, the digestor is a single-stage digestor. Here "single stage" means that biomass is extracted with an extraction solution (e.g., liquid hot water with an optional acid such as acetic acid) at reaction temperature and pressure, to solubilize hemicelluloses and lignin, with no intermediate separation prior to entering a mechanical refiner, blow line, or blow valve. The hemicelluloses are not separated and the cellulose-rich solids are not separately processed prior to enzymatic hydrolysis. Following the digestor and optional blow-line refiner, and after the pressure is released to reach atmospheric pressure, in some embodiments, the hemicelluloses may be washed from the solids and separately processed to hydrolyze hemicelluloses to monomers and/or to separately ferment hemicellulose sugars to ethanol. In some embodiments, there is no intermediate separation: all extracted/digested contents—both the solid and liquid phases—are sent to enzymatic hydrolysis to produce glucose and other monomer sugars such as xylose.

Some specific embodiments of the invention employ a single-stage vertical digestor configured to continuously pretreat incoming biomass with liquid hot water, followed by blow-line refining of the entire pretreated material, and then followed by enzymatic hydrolysis of the entire refined material.

The mechanical refiner may be selected from the group consisting of a hot-blow refiner, a hot-stock refiner, a blow-line refiner, a disk refiner, a conical refiner, a cylindrical refiner, an in-line defibrator, a homogenizer, and combinations thereof (noting that these industry terms are not mutually exclusive to each other). In certain embodiments, the mechanical refiner is a blow-line refiner. Other mechanical refiners may be employed, and chemical refining aids (e.g., fatty acids) may be introduced, such as to adjust viscosity, density, lubricity, etc.

Mechanically treating (refining) may employ one or more known techniques such as, but by no means limited to, milling, grinding, beating, sonicating, or any other means to reduce cellulose particle size. Such refiners are well-known in the industry and include, without limitation, Valley beaters, single disk refiners, double disk refiners, conical refiners, including both wide angle and narrow angle, cylindrical refiners, homogenizers, microfluidizers, and other similar milling or grinding apparatus. See, for example, Smook, *Handbook for Pulp & Paper Technologists*, Tappi Press, 1992.

A pressurized refiner may operate at the same pressure as the digestor, or at a different pressure. In some embodiments, both the digestor and the refiner operate in a pressure range corresponding to equilibrium steam saturation temperatures from about 170° C. to about 210° C., such as about 180° C. to about 200° C. In some embodiments, a pressurized refiner is fed by a screw between the digestor and the refiner.

In principle, the pressure in the refiner could be higher than the digestor pressure, due to mechanical energy input. For example, a high-pressure screw feeder could be utilized to increase refining pressure, if desired. Also, it will be recognized that localized pressures (force divided by area) may be higher than the vapor pressure, due to the presence of mechanical surface force (e.g., plates) impacting the solid material or slurry.

A blow tank may be situated downstream of the mechanical refiner, so that the mechanical refiner operates under pressure. The pressure of the mechanical refiner may be the same as the digestor pressure, or it may be different. In some embodiments, the mechanical refiner is operated at a refining pressure selected from about 30 psig (2.07 bar, noting that "bar" herein refers to gauge pressure) to about 300 psig (20.7 bar), such as about 50 psig (3.45 bar) to about 150 psig (10.3 bar).

A blow tank may be situated upstream of the mechanical refiner, so that the mechanical refiner operates under reduced pressure or atmospheric pressure. In some embodiments, the mechanical refiner is operated a refining pressure of less than about 50 psig, less than about 30 psig, or at or about atmospheric pressure.

Note that "blow tank" should be broadly construed to include not only a tank but any other apparatus or equipment capable of allowing a pressure reduction in the process stream. Thus a blow tank may be a tank, vessel, section of pipe, valve, separation device, or other unit.

In some embodiments, following a digestor to remove hemicellulose, an intermediate blow is performed to, for example, about 40 psig. The material is sent to a blow-line refiner, and then to a final blow to atmospheric pressure, for example. In some embodiments, a cold blow discharger is utilized to feed a pressurized refiner. In some embodiments, a transfer conveyor is utilized to feed a pressurized refiner.

The refining may be conducted at a wide range of solids concentrations (consistency), including from about 2% to about 50% consistency, such as about 4%, 6%, 8%, 10%, 15%, 20%, 30%, 35%, or 40% consistency.

A pressurized refiner may operate at the same pressure as the digestor, or at a different pressure. In some embodiments, both the digestor and the refiner operate in a pressure range corresponding to equilibrium steam saturation temperatures from about 170° C. to about 210° C., such as about 180° C. to about 200° C. In some embodiments, a pressurized refiner is fed by a screw between the digestor and the refiner.

In certain embodiments of the invention, a first blow tank is situated upstream of the mechanical refiner and a second blow tank is situated downstream of the mechanical refiner. In this scenario, the pressure is reduced somewhat between the digestor and the refiner, which operates above atmospheric pressure. Following the refining, the pressure is released in the second blow tank. In some embodiments, the mechanical refiner is operated at a refining pressure selected from about 10 psig to about 150 psig, such as about 20 psig to about 100 psig, or about 30 psig to about 50 psig.

In some embodiments, the vapor is separated from a blow tank, and heat is recovered from at least some of the vapor. At least some of the vapor may be compressed and returned to the digestor. Some of the vapor may be purged from the process.

In some embodiments, heat is recovered from at least some of the vapor, using the principles of heat integration. At least some of the vapor may be compressed and returned to the digestor. Some of the vapor may be purged from the process.

In certain embodiments, the reduction of pressure that occurs across a blow valve causes, or assists, fiber expansion or fiber explosion. Fiber expansion or explosion is a type of physical action that can occur, reducing particle size or surface area of the cellulose phase, and enhancing the enzymatic digestibility of the pretreated cellulose. Certain embodiments employ a blow valve (or multiple blow valves) to replace a mechanical refiner or to augment the refining that results from a mechanical refiner, disposed either before or after such blow valve. Some embodiments combine a mechanical refiner and blow value into a single apparatus that simultaneously refines the cellulose-rich solids while blowing the material to a reduced pressure.

In some embodiments, enzymes introduced or present in the enzymatic hydrolysis unit may include not only cellulases but also hemicellulases. In certain embodiments, enzymes introduced or present in the enzymatic hydrolysis unit include endoglucanases and exoglucanases.

Enzymatic hydrolysis may be conducted at a solids concentration from about 5 wt % to about 25 wt %, such as about 10 wt %, 12 wt %, 15 wt %, 18 wt %, 20 wt %, or 22 wt %.

The enzymatic hydrolysis unit may include a single stage configured for cellulose liquefaction and saccharification, wherein the single stage includes one or more tanks or vessels. Alternatively, the enzymatic hydrolysis unit may include two stages configured for cellulose liquefaction followed by saccharification, wherein each stage includes one or more tanks or vessels.

Enzymes introduced or present in the enzymatic hydrolysis unit may include cellulases and hemicellulases. In some embodiments, enzymes introduced or present in the enzymatic hydrolysis unit include endoglucanases and exoglucanases.

Some embodiments employ two or more enzymatic hydrolysis units. The first enzymatic hydrolysis unit may include a single stage configured for cellulose liquefaction and saccharification, wherein the single stage includes one or more tanks or vessels. Alternatively, the first enzymatic hydrolysis unit may include two stages configured for cellulose liquefaction followed by saccharification, wherein each stage includes one or more tanks or vessels.

The second enzymatic hydrolysis unit may include a single stage configured for cellulose liquefaction and saccharification, wherein the single stage includes one or more tanks or vessels. Alternatively, the second enzymatic hydrolysis unit may include two stages configured for cellulose liquefaction followed by saccharification, wherein each stage includes one or more tanks or vessels. In certain embodiments, the process further comprises recycling at least some material treated in the second enzymatic hydrolysis unit, for solid/liquid separation, for example.

Enzymes introduced or present in the enzymatic hydrolysis unit may include cellulases and hemicellulases. In some embodiments, enzymes introduced or present in the enzymatic hydrolysis unit include endoglucanases and exoglucanases.

The hydrolysis reactor may be configured in one or more stages or vessels. In some embodiments, a hydrolysis reactor is a system of two, three, or more physical vessels which are configured to carry out liquefaction or hydrolysis of sugar oligomers. For example, in certain embodiments, a liquefaction tank is followed by a hydrolysis tank, which is then followed by another tank for extended hydrolysis. Enzymes may be added to any one or more of these vessels, and enzyme recycling may be employed.

In other embodiments, a single physical hydrolysis reactor is utilized, which reactor contains a plurality of zones, such as a liquefaction zone, a first hydrolysis zone, and a second hydrolysis zone. The zones may be stationary or moving, and the reactor may be a continuous plug-flow reactor, a continuous stirred reactor, a batch reactor, a semi-batch reactor, or any combination of these, including arbitrary flow patterns of solid and liquid phases.

A mechanical refiner may be included before liquefaction, between the liquefaction tank and hydrolysis tank, and/or between the hydrolysis tank and the extended hydrolysis tank. Alternatively or additionally, a mechanical refiner may be included elsewhere in the process. Enzymes may be introduced directly into any of the refiners, if desired.

In some embodiments, enzymes are introduced directly to the mechanical refiner. In these or other embodiments, the enzymes are introduced to the digested stream, upstream of the mechanical refiner. The enzymes may include cellulases (e.g., endoglucanases and exoglucanases) and hemicellulases.

The effective hydrolysis conditions may include a maximum temperature of 75° C. or less, preferably 65° C. or less, within the mechanical refiner. In some embodiments, the effective hydrolysis conditions include a hydrolysis temperature of about 30° C., 40° C., 50° C., 60° C., or 70° C. within the mechanical refiner. These are average temperatures within the refining zone. Local hot spots may be present within the refiner, such as in regions of high-shear, high-friction contact between cellulose-rich solids and metal plates.

In some embodiments, a hydrolysis reactor or a refiner is configured to cause at least some liquefaction as a result of enzymatic action on the cellulose-rich solids. "Liquefaction" means partial hydrolysis of cellulose to form glucose oligomers (i.e. glucan) that dissolve into solution, but not total hydrolysis of cellulose to glucose monomers (saccharification). Various fractions of cellulose may be hydrolyzed during liquefaction. In some embodiments, the fraction of cellulose hydrolyzed may be from about 5% to about 90%, such as about 10% to about 75% (e.g. about 15%, 20%, 25%, 30%, 35%, 40%, 45%, 50%, 55%, 60%, 65%, or 70%). In certain embodiments, there is no separate liquefaction tank or reactor; liquefaction and hydrolysis occur in the same vessel (e.g., refiner or hydrolysis reactor).

A "liquefaction-focused blend of enzymes" means a mixture of enzymes that includes at least one enzyme capable of hydrolyzing cellulose to form soluble oligomers. In some embodiments, a liquefaction-focused blend of enzymes includes both endoglucanases and exoglucanases. Endoglucanases are cellulases that attack low-crystallinity regions in the cellulose fibers by endoaction, creating free chain-ends. Exoglucanases or cellobiohydrolases are cellulases that hydrolyze the 1,4-glycocidyl linkages in cellobiose.

Various cellulase enzymes may be utilized in the liquefaction-focused blend of enzymes, such as one or more enzymes recited in Verardi et al., "Hydrolysis of Lignocellulosic Biomass: Current Status of Processes and Technologies and Future Perspectives," *Bioethanol*, Prof. Marco Aurelio Pinheiro Lima (Ed.), ISBN: 978-953-51-0008-9, InTech (2012), which is hereby incorporated by reference.

Some embodiments employ thermotolerant enzymes obtained from thermophilic microrganisms. The thermophilic microrganisms can be grouped in thermophiles (growth up to 60° C.), extreme thermophiles (65-80° C.) and hyperthermophiles (85-110° C.). The unique stability of the enzymes produced by these microrganisms at elevated temperatures, extreme pH and high pressure (up to 1000 bar) makes them valuable for processes at harsh conditions. Also, thermophilic enzymes have an increased resistance to many denaturing conditions such as the use of detergents which can be an efficient means to obviate the irreversible adsorption of cellulases on the substrates. Furthermore, the utilization of high operation temperatures, which cause a decrease in viscosity and an increase in the diffusion coefficients of substrates, have a significant influence on the cellulose solubilization. Most thermophilic cellulases do not show inhibition at high level of reaction products (e.g. cellobiose and glucose). As consequence, higher reaction rates and higher process yields are expected. The high process temperature also reduces contamination. See Table 6, "Thermostable cellulases" in Verardi et al., cited above, for exemplary thermotolerant enzymes that may be used in the liquefaction-focused blend of enzymes, or in other embodiments herein In some embodiments, an enzyme is selected such that at a high temperature, the enzyme is able to catalyze liquefaction (partial hydrolysis) but not saccharification (total hydrolysis). When the temperature is reduced, the same enzyme is able to catalyze saccharification to produce glucose.

When the hydrolysis process employs enzymes, these enzymes will typically contain cellulases and hemicellulases. The cellulases here may include β-glucosidases that convert cellooligosaccharides and disaccharide cellobiose into glucose. There are a number of enzymes that can attack hemicelluloses, such as glucoronide, acetylesterase, xylanase, β-xylosidase, galactomannase and glucomannase. Exemplary acid catalysts include sulfuric acid, sulfur dioxide, hydrochloric acid, phosphoric acid, and nitric acid.

In certain embodiments of the invention, a self-cleaning filter is configured downstream of a hydrolysis tank to remove cellulose fiber strands prior to sending the hydrolysate to a fermentor or other unit (e.g., another hydrolysis vessel for extended hydrolysis of soluble material). The self-cleaning filter continuously rejects solids (including cellulose fiber strands) that may be recycled back to the first hydrolysis vessel. For example, the cellulose fiber strands may be recycled to a biomass cooler that feeds a viscosity-reduction tank at the beginning of hydrolysis.

Many fluid streams contain particulate matter, and it is often desirable to separate this particulate matter from the fluid stream. If not separated, the particulate matter may degrade product quality, efficiency, reduce performance, or cause severe damage to components within the system. Many types of filters have been designed for the purpose of removing particulate matter from fluid streams. Such filters have typically included a filter element designed to screen the particulate material. However, the particulate material often becomes entrapped in the filter element. As the quantity of particulate material, often referred to as filter cake, collects on the filter element, the pressure drop that occurs across the filter element increases. A pressure drop across the filter element of sufficient magnitude can significantly reduce fluid flow at which point the filter element must be periodically cleaned, or replaced with a new filter. Often, this is done manually by removing the filter element and cleaning the filter before reinstalling it back in the system. To minimize manual operations, filters have been designed to accomplish continuous self-cleaning.

As intended herein, a "self-cleaning filter" should be construed broadly to refer to self-cleaning filtration devices, self-cleaning decanters, self-cleaning screens, self-cleaning centrifuges, self-cleaning cyclones, self-cleaning rotary drums, self-cleaning extruders, or other self-cleaning separation devices.

Some self-cleaning filters use back pulsing to dislodge materials or blades to scrape off caked particulate. Some self-cleaning filters are cleaned with sprayed fluids, such as water or air to remove the particulates. Some self-cleaning filters utilize high pressures or forces to dislodge caked particulate from the filter. Some self-cleaning filters employ a moving (e.g., rotating) filter design wherein particulates are continuously filtered and removed due to centrifugal force or other forces. Many self-cleaning filters are available commercially.

Also see, for example, U.S. Pat. No. 4,552,655, issued Nov. 12, 1985 and U.S. Pat. No. 8,529,661, issued Sep. 10, 2013, which are hereby incorporated by reference as prior art for self-cleaning filters.

As intended herein, "cellulose fiber strands" generally refer to relatively large, non-soluble cellulose-containing particles in the form of individual fibers or bundles of fibers. Cellulose fiber strands, without limitation, may have lengths or effective lengths in the range of about 0.1 mm to about 10 mm, such as about 0.5 mm to about 5 mm. Some fiber strand bundles may have very large length or particle size, such as about 10 mm or more. The principles of the invention may be applied to smaller cellulose particles, with length or particle size less than 0.1 mm, as long as the particles can be captured by a self-cleaning filter.

In some embodiments, the composition of some cellulose fiber strands may be similar to the composition of the starting biomass material, such as when large particles were not effectively pretreated in the digestor.

In some embodiments, a self-cleaning filter is configured downstream of an enzymatic hydrolysis unit to remove cellulosic fiber strands. The self-cleaning filter is preferably operated continuously. The cellulosic fiber strands may be recycled back to one or more of the one or more enzymatic hydrolysis units, for further cellulose hydrolysis.

In some embodiments of the invention, a self-cleaning filter is configured downstream of the enzymatic liquefaction unit to remove cellulosic fiber strands. In these or other embodiments, a self-cleaning filter is configured downstream of the first enzymatic hydrolysis unit to remove cellulosic fiber strands. In these or other embodiments, a self-cleaning filter is configured downstream of the second enzymatic hydrolysis unit to remove cellulosic fiber strands.

At least a portion of the cellulosic fiber strands may be recycled back to the enzymatic liquefaction unit or to vessel or heat exchanger that feeds into the enzymatic liquefaction unit. Alternatively, or additionally, at least a portion of the cellulosic fiber strands are recycled back to the first enzymatic hydrolysis unit or to vessel or heat exchanger that feeds into the first enzymatic hydrolysis unit. Alternatively, or additionally, at least a portion of the cellulosic fiber strands are recycled back to the digestor and/or to one of the mechanical refiners.

Generally speaking, the enzymatic hydrolysis that follows the hydrothermal-mechanical process should be optimized for the biomass type, the capital cost of tanks versus solids content, energy integration with the rest of the plant, and enzyme cost versus sugar yield. For each commercial implementation, one skilled in the art may carry out a design of experiments in cooperation with an enzyme supplier, or in conjunction with on-site enzyme production. In some embodiments, a process disclosed herein is retrofitted to an existing digestor, and existing refiner, an existing hydrolysis reactor, and/or an existing fermentation system. Such a retrofit needs to adapt to site constraints.

The process may further include removal of one or more fermentation inhibitors by stripping. This stripping may be conducted following step (e), i.e. treating the hydrolyzed cellulose stream, prior to fermentation. Alternatively, or additionally, the stripping may be conducted on a stream following digestion, such as in the blow line, or as part of an acetic acid recycle system.

The process may further include a step of fermenting the fermentable sugars to a fermentation product. Typically the process will further include concentration and purification of the fermentation product. The fermentation product may be selected from ethanol, n-butanol, 1,4-butanediol, succinic acid, lactic acid, or combinations thereof, for example. The lignin may be combusted for energy production.

Some embodiments further include removing a solid stream containing lignin following prior to fermentation of the fermentable sugars. In these or other embodiments, the process may further include removing a solid stream containing lignin following fermentation of the fermentable sugars. The lignin may be combusted or used for other purposes.

Some variations described herein are premised on the design of process options to increase the yield of ethanol production (or other fermentation product). Some process configurations include sending digested pulp, after a hot blow but before any mechanical refining, to continuous enzymatic hydrolysis. The enzymatic hydrolysis may be configured in one step (liquefaction and saccharification in one vessel) or two steps (tanks) in series. The different vessels may be designed/operated as continuous stirred tank reactors. The material (liquid and solid) from the enzymatic hydrolysis may undergo a solid/liquid separation, wherein the liquid phase containing $C_5$ and $C_6$ sugars is sent to fermentation. The solid phase may be sent to an atmospheric pulp refiner wherein further deconstruction of the non-hydrolyzed fiber (solid phase) is achieved by adjusting the refiner power load and physical parameters (e.g., dimensions of gaps or grooves). Next, the refined fiber is sent to another enzymatic hydrolysis unit or is recycled back to the primary hydrolysis unit. These embodiments may increase enzymatic hydrolysis yield by recycling more deconstructed fiber, and/or increase fiber digestibility to fermentation microorganisms which translates into higher ethanol yield. Less solids sent to fermentation translates to higher fermentation yield. A cleaner fermentation beer which will produce less fouling of the beer column.

In some variations, a process for producing fermentable sugars from cellulosic biomass comprises:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) reducing pressure of the digested stream;

(d) introducing the digested stream to an enzymatic hydrolysis unit under effective hydrolysis conditions to produce a liquid phase comprising sugars from the cellulose-rich solids and optionally from the hemicellulose oligomers, and a solid phase comprising the cellulose-rich solids;

(e) separating the liquid phase and the solid phase from step (d);

(f) conveying the solid phase through a mechanical refiner, thereby generating a refined stream with reduced average particle size of the cellulose-rich solids;

(g) recycling the refined stream to the enzymatic hydrolysis unit, to produce additional sugars from the cellulose-rich solids contained in the solid phase from step (d); and (h) recovering or further processing at least some of the sugars and at least some of the additional sugars as fermentable sugars.

Other variations provide a process for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) reducing pressure of the digested stream;

(d) introducing the digested stream to a first enzymatic hydrolysis unit under effective hydrolysis conditions to produce a liquid phase comprising sugars from the cellulose-rich solids and optionally from the hemicellulose oligomers, and a solid phase comprising the cellulose-rich solids;

(e) separating the liquid phase and the solid phase from step (d);

(f) conveying the solid phase through a mechanical refiner, thereby generating a refined stream with reduced average particle size of the cellulose-rich solids;

(g) recycling the refined stream to a second enzymatic hydrolysis unit, to produce additional sugars from the cellulose-rich solids contained in the solid phase from step (d); and (h) recovering or further processing at least some of the sugars and/or the additional sugars as fermentable sugars.

Some variations provide a process for producing fermentable sugars from cellulosic biomass, the process comprising:

(a) providing a feedstock comprising cellulosic biomass;

(b) digesting the feedstock with a reaction solution including steam and/or hot water in a digestor under effective reaction conditions to produce a digested stream containing cellulose-rich solids, hemicellulose oligomers, and lignin;

(c) optionally conveying the digested stream through a mechanical refiner, thereby generating a refined stream with reduced average particle size of the cellulose-rich solids;

(d) introducing the digested stream and/or (if step (c) is conducted) the refined stream to an enzymatic hydrolysis unit under effective hydrolysis conditions to produce a sugar-containing hydrolysate;

(e) evaporating the hydrolysate using a multiple-effect evaporator or a mechanical vapor compression evaporator, to produce a concentrated hydrolysate;

(f) fermenting the concentrated hydrolysate to produce a dilute fermentation product; and (g) concentrating the dilute fermentation product to produce a concentrated fermentation product.

Step (d) may be conducted at a solids concentration from about 5 wt % to about 25 wt %, such as about 10 wt %, 15 wt %, or 20 wt %.

Step (g) may utilize distillation, which generates a distillation bottoms stream. In some embodiments, the distillation bottoms stream is evaporated in a distillation bottoms evaporator that is integrated with step (e) in a multiple-effect evaporator train. The distillation bottoms evaporator may provide lignin-rich combustion fuel.

Suspended solids (lignin or other solids) may be removed prior to step (e). In some embodiments, suspended solids are during or after step (e) and prior to the distillation bottoms evaporator.

The concentrated fermentation product may be selected from ethanol, n-butanol, isobutanol, 1,4-butanediol, succinic acid, lactic acid, or combinations thereof, for example. In certain embodiments, the concentrated fermentation product is ethanol.

In some embodiments, the process includes washing the cellulose-rich solids using an aqueous wash solution, to produce a wash filtrate; and optionally combining at least some of the wash filtrate with the extract liquor. In some of these embodiments, the process further includes pressing the cellulose-rich solids to produce the washed cellulose-rich solids and a press filtrate; and optionally combining at least some of the press filtrate with the extract liquor.

The process may include countercurrent washing, such as in two, three, four, or more washing stages. The separation/washing may be combined with the application of enzymes, in various ways.

Two hydrolysis catalysts may be utilized in series. In some embodiments, a first hydrolysis catalyst includes cellulases. In some embodiments, a second hydrolysis catalyst includes hemicellulases. In other embodiments, the first hydrolysis catalyst and the second hydrolysis catalyst are acid catalysts, base catalysts, ionic liquids, solid catalysts, or other effective materials. The first hydrolysis catalyst may be the same as, or different than, the second hydrolysis catalyst.

In some embodiments, the glucose is recovered in a separate stream from the hemicellulose monomers. In other embodiments, the glucose and the hemicellulose monomers are recovered in the same stream. The process may include fermentation of the glucose and/or the fermentable hemicellulose sugars to a fermentation product.

In some embodiments, the process starts as biomass is received or reduced to a desired particle size. In a first step of the process, the biomass is fed (e.g., from a feed bin) to a pressurized extraction vessel operating continuously or in batch mode. The biomass may first be steamed or water-washed to remove dirt and entrained air. The biomass is immersed with aqueous liquor or saturated vapor and heated to a temperature between about 100° C. to about 250° C., for example 150° C., 160° C., 170° C., 180° C., 190° C., 200° C., or 210° C. Preferably, the biomass is heated to about 180° C. to 210° C.

The pressure in the pressurized vessel may be adjusted to maintain the aqueous liquor as a liquid, a vapor, or a combination thereof. Exemplary pressures are about 1 bar to about 30 bar, such as about 3 bar, 5 bar, 10 bar, or 15 bar.

The solid-phase residence time for the digestor (pressurized extraction vessel) may vary from about 2 minutes to about 4 hours, such as about 5 minutes to about 1 hour. In certain embodiments, the digestor residence time is controlled to be about 5 to 15 minutes, such as 5, 6, 7, 8, 9, 10, 11, 12, 13, 14 or 15 minutes. The liquid-phase residence time for the digestor may vary from about 2 minutes to about 4 hours, such as about 5 minutes to about 1 hour. The vapor-phase residence time for the digestor may vary from about 1 minute to about 2 hours, for example, such as about 3 minutes to about 30 minutes. The solid-phase, liquid-phase, and vapor-phase residence times may all be about the same, or they may be independently controlled according to reactor-engineering principles (e.g., recycling and internal recirculation strategies).

The aqueous liquor may contain acidifying compounds, such as (but not limited to) sulfuric acid, sulfurous acid, sulfur dioxide, acetic acid, formic acid, or oxalic acid, or combinations thereof. The dilute acid concentration (if any) can range from 0.01 wt % to 10 wt % as necessary to improve solubility of particular minerals, such as potassium, sodium, or silica. Preferably, the acid concentration is selected from about 0.01 wt % to 4 wt %, such as 0.1 wt %, 0.5 wt %, or 1 wt %.

A second step may include depressurization of the extracted biomass into a blow tank or other tank or unit. The vapor can be used for heating the incoming biomass or cooking liquor, directly or indirectly. The volatilized organic acids (e.g., acetic acid), which are generated or included in the cooking step, may be recycled back to the cooking.

A third step may include mechanically refining the extracted biomass. This step (using, for example, a blow-line refiner) may be done before or after depressurization.

Optionally, refined solids may be washed. The washing may be accomplished with water, recycled condensates, recycled permeate, or a combination thereof. Washing typically removes most of the dissolved material, including hemicelluloses and minerals. The final consistency of the dewatered cellulose-rich solids may be increased to 30% or more, preferably to 50% or more, using a mechanical pressing device. The mechanical pressing device may be integrated with the mechanical refiner, to accomplish combined refining and washing.

A fourth step may include hydrolyzing the extracted chips with enzymes to convert some of the cellulose to glucose. When enzymes are employed for the cellulose hydrolysis, the enzymes preferably include cellulase enzymes. Enzymes may be introduced to the extracted chips along with water, recycled condensates, recycled permeate, additives to adjust pH, additives to enhance hydrolysis (such as lignosulfonates), or combinations thereof.

Some or all of the enzymes may be added to the blow line before or at the blow-line refiner, for example, to assist in enzyme contact with fibers. In some embodiments, at least a portion of enzymes are recycled in a batch or continuous process.

When an acid is employed for the cellulose hydrolysis, the acid may be selected from sulfuric acid, sulfurous acid, sulfur dioxide, formic acid, acetic acid, oxalic acid, or combinations thereof. Acids may be added to the extracted chips before or after mechanical refining. In some embodiments, dilute acidic conditions are used at temperatures between about 100° C. and 190° C., for example about 120° C., 130° C., 140° C., 150° C., 160° C., or 170° C., and preferably from 120° C. to 150° C. In some embodiments, at least a portion of the acid is recycled in a batch or continuous process.

The acid may be selected from sulfuric acid, sulfurous acid, or sulfur dioxide. Alternatively, or additionally, the acid may include formic acid, acetic acid, or oxalic acid from the cooking liquor or recycled from previous hydrolysis.

A fifth step may include conditioning of hydrolysate to remove some or most of the volatile acids and other fermentation inhibitors. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to the first step (cooking step) to assist in the removal of hemicelluloses or minerals from the biomass. This recycle of organic acids, such as acetic acid, may be optimized along with process conditions that may vary depending on the amount recycled, to improve the cooking effectiveness.

A sixth step may include recovering fermentable sugars, which may be stored, transported, or processed. A sixth step may include fermenting the fermentable sugars to a product, as further discussed below.

A seventh step may include preparing the solid residuals (containing lignin) for combustion. This step may include refining, milling, fluidizing, compacting, and/or pelletizing the dried, extracted biomass. The solid residuals may be fed to a boiler in the form of fine powder, loose fiber, pellets, briquettes, extrudates, or any other suitable form. Using known equipment, solid residuals may be extruded through a pressurized chamber to form uniformly sized pellets or briquettes.

In some embodiments, the fermentable sugars are recovered from solution, in concentrated form. In some embodiments, the fermentable sugars are fermented to produce of biochemicals or biofuels such as (but by no means limited to) ethanol, 1-butanol, isobutanol, acetic acid, lactic acid, or any other fermentation products. A purified fermentation product may be produced by distilling the fermentation product, which will also generate a distillation bottoms stream containing residual solids. A bottoms evaporation stage may be used, to produce residual solids.

Following fermentation, residual solids (such as distillation bottoms) may be recovered, or burned in solid or slurry form, or recycled to be combined into the biomass pellets. Use of the fermentation residual solids may require further removal of minerals. Generally, any leftover solids may be used for burning, after concentration of the distillation bottoms.

Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

In certain embodiments, the process further comprises combining, at a pH of about 4.8 to 10 or higher, a portion of vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered. If desired, purified acetic acid may be generated from the alkaline acetate.

In some variations, fermentation inhibitors are separated from a biomass-derived hydrolysate, such as by the following steps:

(a) providing a biomass-derived liquid hydrolysate stream comprising a fermentation inhibitor;

(b) introducing the liquid hydrolysate stream to a stripping column;

(c) introducing a steam-rich vapor stream to the stripping column to strip at least a portion of the fermentation inhibitor from the liquid hydrolysate stream;

(d) recovering, from the stripping column, a stripped liquid stream and a stripper vapor output stream, wherein the stripped liquid stream has lower fermentation inhibitor concentration than the liquid hydrolysate stream;

(e) compressing the stripper vapor output stream to generate a compressed vapor stream;

(f) introducing the compressed vapor stream, and a water-rich liquid stream, to an evaporator;

(g) recovering, from the evaporator, an evaporated liquid stream and an evaporator output vapor stream; and (h) recycling at least a portion of the evaporator output vapor stream to the stripping column as the steam-rich vapor stream, or a portion thereof.

The biomass-derived hydrolysate may be the product of acidic or enzymatic hydrolysis, or it may be the extracted solution from the digestor, for example. In some embodiments, the fermentation inhibitor is selected from the group consisting of acetic acid, formic acid, formaldehyde, acetaldehyde, lactic acid, furfural, 5-hydroxymethylfurfural, furans, uronic acids, phenolic compounds, sulfur-containing compounds, and combinations or derivatives thereof.

In some embodiments, the water-rich liquid stream contains biomass solids that are concentrated in the evaporator. These biomass solids may be derived from the same biomass feedstock as is the biomass-derived liquid hydrolysate, in an integrated process.

Optionally, the fermentation inhibitor is recycled to a previous unit operation (e.g., digestor or reactor) for generating the biomass-derived liquid hydrolysate stream, to assist with hydrolysis or pretreatment of a biomass feedstock or component thereof. For example, acetic acid may be recycled for this purpose, to aid in removal of hemicelluloses from biomass and/or in oligomer hydrolysis to monomer sugars.

Some variations provide a process for separating fermentation inhibitors from a biomass-derived hydrolysate, the process comprising:

(a) providing a biomass-derived liquid hydrolysate stream comprising a fermentation inhibitor;

(b) introducing the liquid hydrolysate stream to a stripping column;

(c) introducing a steam-rich vapor stream to the stripping column to strip at least a portion of the fermentation inhibitor from the liquid hydrolysate stream;

(d) recovering, from the stripping column, a stripped liquid stream and a stripper vapor output stream, wherein the stripped liquid stream has lower fermentation inhibitor concentration than the liquid hydrolysate stream;

(e) introducing the stripper vapor output stream, and a water-rich liquid stream, to an evaporator;

(f) recovering, from the evaporator, an evaporated liquid stream and an evaporator output vapor stream;

(g) compressing the evaporator output vapor stream to generate a compressed vapor stream; and (h) recycling at least a portion of the compressed vapor stream to the stripping column as the steam-rich vapor stream, or a portion thereof.

In some embodiments, the evaporator is a boiler, the water-rich liquid stream comprises boiler feed water, and the evaporated liquid stream comprises boiler condensate.

The process may be continuous, semi-continuous, or batch. When continuous or semi-continuous, the stripping column may be operated countercurrently, cocurrently, or a combination thereof.

In certain variations, a process for separating and recovering a fermentation inhibitor from a biomass-derived hydrolysate comprises:

(a) providing a biomass-derived liquid hydrolysate stream comprising a fermentation inhibitor;

(b) introducing the liquid hydrolysate stream to a stripping column;

(c) introducing a steam-rich vapor stream to the stripping column to strip at least a portion of the fermentation inhibitor from the liquid hydrolysate stream;

(d) recovering, from the stripping column, a stripped liquid stream and a stripper vapor output stream, wherein the stripped liquid stream has lower fermentation inhibitor concentration than the liquid hydrolysate stream;

(e) introducing the stripper vapor output stream, and a water-rich liquid stream, to a rectification column;

(f) recovering, from the rectification column, a rectified liquid stream and a rectification column vapor stream, wherein the rectified liquid stream has higher fermentation inhibitor concentration than the liquid hydrolysate stream; and (g) recycling at least a portion of the rectification column vapor stream to the stripping column as the steam-rich vapor stream, or a portion thereof.

The fermentation inhibitor may be selected from the group consisting of acetic acid, formic acid, formaldehyde, acetaldehyde, lactic acid, furfural, 5-hydroxymethylfurfural, furans, uronic acids, phenolic compounds, sulfur-containing compounds, and combinations or derivatives thereof. In some embodiments, the fermentation inhibitor comprises or consists essentially of acetic acid.

In the case of acetic acid, the stripped liquid stream preferably has less than 10 g/L acetic acid concentration, such as less than 5 g/L acetic acid concentration. The rectification column vapor stream preferably has less than 0.5 g/L acetic acid concentration, such as less than 0.1 g/L acetic acid concentration. The rectified liquid stream preferably has at least 25 g/L acetic acid concentration, such as about 40 g/L or more acetic acid. In some embodiments, the rectified liquid stream has at least 10 times higher concentration of acetic acid compared to the stripped liquid stream. In certain embodiments, the process further comprises recovering the acetic acid contained in the rectified liquid stream using liquid-vapor extraction or liquid-liquid extraction.

In some embodiments, the water-rich liquid stream includes evaporator condensate. The evaporator condensate may be derived from an evaporator in which biomass solids are concentrated, and the biomass solids may be derived from the same biomass feedstock as the biomass-derived liquid hydrolysate, in an integrated process.

Optionally, the fermentation inhibitor (e.g., acetic acid) is recycled to a previous unit operation for generating the biomass-derived liquid hydrolysate stream, to assist with hydrolysis or pretreatment of a biomass feedstock or component thereof.

The process may be continuous, semi-continuous, or batch. When continuous or semi-continuous, the stripping column may be operated countercurrently, cocurrently, or a combination thereof. The rectification column may be operated continuously or in batch.

In various embodiments, step (g) comprises compressing and/or conveying the rectification column vapor stream using a device selected from the group consisting of a mechanical centrifugal vapor compressor, a mechanical axial vapor compressor, a thermocompressor, an ejector, a diffusion pump, a turbomolecular pump, and combinations thereof.

If desired, a base or other additive may be included in the water-rich liquid stream, or separately introduced to the rectification column, to produce salts or other reaction products derived from fermentation inhibitors. In some embodiments, the water-rich liquid stream includes one or more additives capable of reacting with the fermentation inhibitor. In certain embodiments, the fermentation inhibitor includes acetic acid, and the one or more additives include a base. An acetate salt may then be generated within the rectification column, or in a unit coupled to the rectification column. Optionally, the acetate salt may be separated and recovered using liquid-vapor extraction or liquid-liquid extraction.

A product-by-process is provided by the present invention. That is, some embodiments provide a product, such as ethanol, produced by any of the disclosed processes.

It should be noted that some embodiments utilize a business system in which steps of a selected process are practiced at different sites and potentially by different corporate entities, acting in conjunction with each other in some manner, such as in a joint venture, an agency relationship, a toll producer, a customer with restricted use of product, etc. For example, biomass may be digested and refined by hydrothermal-mechanical steps as described herein, and the refined cellulose-rich solids may be transported to another site for enzymatic hydrolysis to sugars and then fermentation to ethanol. Or the biomass may be digested and refined by hydrothermal-mechanical steps and hydrolyzed by enzymes, and then the hydrolysate is transported to another site (such as a first-generation ethanol plant) to be fermented to ethanol.

Some variations of the invention are known as Green-Power3+® technology or GP3+® technology (trademarks of API Intellectual Property Holdings, LLC), commonly assigned with the assignee of this patent application.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

EXAMPLE

Corn stover is subjected to the process according to some embodiments. The composition of the corn stover is as follows:
Glucan 42.9 wt %
Xylan 21.2 wt %
Galactan 1.2 wt %
Arabinan 2.2 wt %
Mannan 0.2 wt %
Lignin 23.4 wt %
Ash 3.1 wt %

The cook (digestor) conditions include a digestor temperature of 183° C. and a digestor residence time of 22 minutes. Following the chemical reaction in the digestor, light mechanical refining is carried out on the digested material, without separation of solid and liquid. The mechanical refining employs an atmospheric bench refiner (0.5 mm gap, 1 pass).

The digested material is then subjected to enzymatic hydrolysis. The slurry concentration is about 10 wt % total solids. A commercially available cellulase enzyme cocktail is used, at an enzyme dose of 2.25 wt % on biomass. The pH during enzymatic hydrolysis is in the 4.8-5.3 range. The temperature during enzymatic hydrolysis is 54° C., and the hydrolysis is carried out for 72 hours to obtain a liquid hydrolysate.

The liquid hydrolysate is then fermented using a commercially available ethanol-producing yeast. The initial pitch is 0.4 g dry yeast per liter of the time-final fermentation broth. Fed-batch fermentation is employed, with a 20-hour feed time. The total fermentation time is 36 hours, including the fed-batch fill time. Ammonia base is used and the pH is controlled to 6.0. No fermentation nutrients are added during fermentation.

The liquid hydrolysate is fermented to ethanol with 82% theoretical fermentation yield, based on total monomers in the liquid hydrolysate fed to the fermentor. The calculated yield of ethanol is this experiment is about 57 gallons ethanol per dry ton of starting biomass (corn stover).

What is claimed is:

1. A process to produce ethanol from lignocellulosic biomass, said process comprising:
   (a) introducing a lignocellulosic biomass feedstock to a single-stage digestor, wherein said feedstock contains cellulose, hemicellulose, and lignin;
   (b) exposing said feedstock to a reaction solution comprising steam or liquid hot water within said single-stage digestor, to solubilize at least a portion of said hemicellulose in a liquid phase and to provide a cellulose-rich solid phase;
   (c) enzymatically hydrolyzing said cellulose-rich solid phase in a first hydrolysis reactor configured for cellulose liquefaction, thereby providing a first hydrolyzed cellulose mixture containing said liquid phase;
   (d) refining said first hydrolyzed cellulose mixture in a mechanical refiner to reduce average particle size of said first hydrolyzed cellulose mixture, thereby providing a second hydrolyzed cellulose mixture;
   (e) enzymatically hydrolyzing said second hydrolyzed cellulose mixture in a second hydrolysis reactor configured for cellulose saccharification, thereby generating fermentable sugars, wherein said second hydrolysis reactor includes a self-cleaning filter to remove cellulosic fiber strands;
   (f) recycling at least a portion of said cellulosic fiber strands back to said first hydrolysis reactor and/or to said mechanical refiner; and
   (g) fermenting at least some of said fermentable sugars in a fermentor to produce ethanol,
   wherein there is no separation of said liquid phase from said cellulose-rich solid phase between step (b) and step (c).

2. The process of claim 1, wherein said lignocellulosic biomass feedstock is selected from the group consisting of hardwoods, softwoods, sugarcane bagasse, sugarcane straw, energy cane, corn stover, corn cobs, corn fiber, and combinations thereof.

3. The process of claim 1, wherein said lignocellulosic biomass feedstock is pretreated, prior to step (a), using one or more techniques selected from the group consisting of cleaning, washing, presteaming, drying, milling, particle size-classifying, and combinations thereof.

4. The process of claim 1, wherein at least a portion of said reaction solution is introduced to said feedstock in a pre-impregnator prior to step (b).

5. The process of claim 1, wherein step (b) includes a digestor residence time from about 2 minutes to about 4 hours.

6. The process of claim 1, wherein step (b) includes a digestor temperature from about 150° C. to about 220° C.

7. The process of claim 1, wherein step (b) is conducted at a digestor liquid-solid weight ratio from about 1 to about 4.

8. The process of claim 1, wherein step (b) is conducted at a digestor pH from about 3 to about 5.

9. The process of claim 1, wherein said reaction solution further comprises acetic acid.

10. The process of claim 1, wherein vapor is separated from said liquid phase prior to step (c).

11. The process of claim 10, wherein heat is recovered from at least some of said vapor.

12. The process of claim 10, wherein at least some of said vapor is condensed or compressed and returned to said digestor.

13. The process of claim 1, wherein said mechanical refiner is selected from the group consisting of a hot-blow refiner, a hot-stock refiner, a blow-line refiner, a disk refiner, a conical refiner, a cylindrical refiner, an in-line defibrator, an extruder, a homogenizer, and combinations thereof.

14. The process of claim 1, wherein said second hydrolysis reactor is a multiple-stage hydrolysis reactor.

15. The process of claim 1, wherein said self-cleaning filter is disposed between two stages of said multiple-stage hydrolysis reactor.

16. The process of claim 1, wherein step (e) includes enzymatic hydrolysis of hemicellulose oligomers to generate fermentable monomer sugars.

17. The process of claim 16, wherein at least a portion of said fermentable monomer sugars are also fermented to produce said ethanol.

18. The process of claim 1, said process further comprising concentrating said ethanol by distillation.

* * * * *